United States Patent
Kondoh et al.

(10) Patent No.: US 7,625,681 B2
(45) Date of Patent: Dec. 1, 2009

(54) ASYMMETRIC BIS-HYDROXYENAMINE COMPOUND, ELECTROPHOTOGRAPHIC PHOTORECEPTOR AND IMAGE FORMING APPARATUS

(75) Inventors: Akihiro Kondoh, Nara (JP); Hiroshi Sugimura, Habikino (JP); Takatsugu Obata, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 490 days.

(21) Appl. No.: 11/443,368

(22) Filed: May 31, 2006

(65) Prior Publication Data

US 2006/0275683 A1    Dec. 7, 2006

(30) Foreign Application Priority Data

Jun. 1, 2005    (JP)    ............................ P2005-161841

(51) Int. Cl.
*G03G 15/02*    (2006.01)

(52) U.S. Cl. ........................ 430/58.85; 430/72; 430/73; 430/66; 399/159; 546/329; 546/323; 564/315; 564/316

(58) Field of Classification Search .............. 430/58.85, 430/72, 73, 66; 399/159; 546/329, 323; 564/315, 316

See application file for complete search history.

(56) References Cited

U.S. PATENT DOCUMENTS

| 3,824,099 A | 7/1974 | Champ et al. |
| 4,123,269 A | 10/1978 | Von Hoene et al. |

(Continued)

FOREIGN PATENT DOCUMENTS

JP    52-4188    2/1977

(Continued)

OTHER PUBLICATIONS

Machine translation of JP 2004-269377.*

(Continued)

*Primary Examiner*—Mark A Chapman
(74) *Attorney, Agent, or Firm*—Nixon & Vanderhye P.C.

(57) ABSTRACT

There is provided an organic photoconductive material that can realize an electrophotographic photoreceptor which is not only excellent in charge transporting ability but also excellent in solubility in a solvent and compatibility with a resin and moreover, which is excellent in both electric properties and durability, and the organic photoconductive material that is useful also as a raw material compound for various types of functional materials. An asymmetric bis-hydroxyenamine compound represented by the following structural formula (1aa) is provided. The compound is allowed to be contained in a charge transporting layer or a surface protective layer of an electrophotographic photoreceptor. This leads realization of the electrophotographic photoreceptor which is excellent in electric properties and durability and can stably form an image of high quality being free of an image defect such as a black spot.

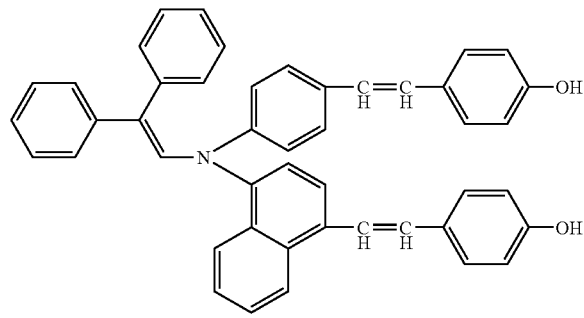

(1aa)

13 Claims, 3 Drawing Sheets

U.S. PATENT DOCUMENTS

| | | | |
|---|---|---|---|
| 4,150,987 A | 4/1979 | Anderson et al. | |
| 4,278,747 A | 7/1981 | Murayama et al. | |
| 4,338,388 A | 7/1982 | Sakai et al. | |
| 4,367,273 A | 1/1983 | Murayama et al. | |
| 4,859,556 A | 8/1989 | Sasaki | |
| 4,892,949 A | 1/1990 | Sasaki | |
| 5,486,439 A | 1/1996 | Sakakibara et al. | |
| 5,639,581 A | 6/1997 | Iwasaki et al. | |
| 5,734,003 A | 3/1998 | Iwasaki et al. | |
| 5,942,363 A | 8/1999 | Tanaka et al. | |
| 6,093,784 A | 7/2000 | Tamura et al. | |
| 6,191,249 B1 | 2/2001 | Tanaka et al. | |
| 6,265,122 B1 | 7/2001 | Itami et al. | |
| 7,416,824 B2 * | 8/2008 | Kondoh et al. | 430/58.85 |
| 2002/0147278 A1 | 10/2002 | Sasaki et al. | |

FOREIGN PATENT DOCUMENTS

| | | |
|---|---|---|
| JP | 54-150128 | 11/1979 |
| JP | 54-151955 | 11/1979 |
| JP | 55-52063 | 4/1980 |
| JP | 55-42380 | 10/1980 |
| JP | 58-32372 | 7/1983 |
| JP | 58-198043 | 11/1983 |
| JP | 2-51162 A | 2/1990 |
| JP | 2-184857 A | 7/1990 |
| JP | 2-190862 | 7/1990 |
| JP | 3-221522 | 9/1991 |
| JP | 4-11627 | 1/1992 |
| JP | 4-120556 A | 4/1992 |
| JP | 6-43674 A | 2/1994 |
| JP | 6-295077 | 10/1994 |
| JP | 7-48324 | 2/1995 |
| JP | 7-228557 | 8/1995 |
| JP | 7-258399 | 10/1995 |
| JP | 8-62864 | 3/1996 |
| JP | 8-95474 A | 4/1996 |
| JP | 8-176293 | 7/1996 |
| JP | 9-194442 | 7/1997 |
| JP | 10-69107 A | 3/1998 |
| JP | 10-239875 A | 9/1998 |
| JP | 10-254153 A | 9/1998 |
| JP | 10-260541 A | 9/1998 |
| JP | 2000-112157 A | 4/2000 |
| JP | 2000-136169 | 5/2000 |
| JP | 2000-242019 | 9/2000 |
| JP | 2002-23396 | 1/2002 |
| JP | 2002-249472 | 9/2002 |
| JP | 2003-176276 A | 6/2003 |
| JP | 2004-217527 | 8/2004 |
| JP | 2004-269377 | 9/2004 |
| JP | 2004-287216 A | 10/2004 |
| JP | 2004-334125 | 11/2004 |
| JP | 2004-354663 A | 12/2004 |

OTHER PUBLICATIONS

English Translation of the International Preliminary Report on Patentability mailed Mar. 23, 2006 in corresponding PCT application No. PCT/JP2004/006590.

International Search Report of PCT/JP2004/006590, mailed Jul. 27, 2004.

Diamond, Arthur S & David Weiss (eds.) Handbook of Imaging Materials, $2^{nd}$ ed., New York: Marcel-Dekker, Inc. (Nov. 2001) pp. 145-164.

JP 3580426, Oct. 20, 2004 corresponds to U.S. Patent No. 7,416,824 (cited by Examiner on PTO-892 attached to Office Action of Dec. 19, 2009).

* cited by examiner

ASYMMETRIC BIS-HYDROXYENAMINE COMPOUND, ELECTROPHOTOGRAPHIC PHOTORECEPTOR AND IMAGE FORMING APPARATUS

BACKGROUND OF THE INVENTION

1. Field of the Invention

The present invention relates to an asymmetrical bis-hydroxyenamine compound, an electrophotographic photoreceptor comprising the asymmetrical bis-hydroxyenamine compound, and an image forming apparatus equipped with the electrophotographic photoreceptor.

2. Description of the Related Art

An electrophotographic image forming apparatus for forming an image through electrophotography (hereinafter referred to also as "electrophotographic apparatus") is much used as copying machines, printers, facsimile apparatus, etc. In the electrophotographic apparatus, an image is formed according to an electrophotographic process as follows. First, the photosensitive layer of an electrophotographic photoreceptor (this may be hereinafter simply referred to also as "photoreceptor") is charged and then exposed to light to thereby form an electrostatic latent image. The thus-formed electrostatic latent image is developed to form a toner image. Thus formed, the toner image is transferred onto a transfer material such as recording paper, and then fixed. According to the process, a desired image is formed on a transfer material.

Recently, electrophotography is utilized not only in the field of printing machines but also in other fields of printing plate materials, slide films, microfilms and others for which silver salt photography has heretofore been used, and in addition, it is further applied to high-speed printers using a light source of laser, light-emitting diode (abbreviated as LED), cathode ray tube (abbreviated as CRT) or the like. With the expansion of the application field of electrophotography, requirements for electrophotographic photoreceptors are being high-leveled and broadened.

As the electrophotographic photoreceptor, conventionally broadly used is an inorganic photoreceptor equipped with a photosensitive layer comprising, as the main ingredient thereof, an inorganic photoconductive material such as selenium, zinc oxide or cadmium sulfide. The inorganic photoreceptor has basic properties as a photoreceptor in some degree, but has some drawbacks in that the film formation for the photosensitive layer is difficult, the plasticity is not good and the production costs are high. In addition, in general, inorganic photoconductive materials are highly toxic, and are therefore greatly limited in point of their production and use.

As described above, since the inorganic photoconductive material and the inorganic photoreceptor using the same involve many drawbacks, research and development have been progressed for organic photoconductive materials. Further, the organic photoconductive material has been studied and developed generally in recent years and it has been utilized not only for electrostatic recording devices such as the electrophotographic photoreceptor but also has been applied, for example, to sensor devices or organic Electro Luminescent (abbreviated as EL) devices.

The organic photoreceptor using the organic photoconductive material has advantages such that the film formation property for the photosensitive layer is favorable and the flexibility is excellent, as well as it is light in the weight, excellent in the transparency, and a photoreceptor showing good sensitivity to a wavelength region over a wide range can be designed easily by an appropriate sensitizing method. Thus, the organic photoreceptor has been under development as a predominant candidate for the electrophotographic photoreceptor.

In the early days, organic photoreceptors had some drawbacks in point of the sensitivity and the durability thereof, but these drawbacks have been significantly improved by development of a function-separated electrophotographic photoreceptor of which the charge generating function and the charge transporting function are separately attained by different substances. The function-separated photoreceptor of the type has, in addition to the above-mentioned advantages of organic photoreceptors, other advantages in that it has broad latitude in selecting the materials for the photosensitive layer and those having any desired characteristics are relatively readily produced.

The function-separated photoreceptor is grouped into a layered type photoreceptor and a single layer type photoreceptor. In the single layer type function-separated photoreceptor, provided is a single layer type photosensitive layer where a charge generating substance having a charge generating function and a charge transporting substance having a charge transporting function are co-dispersed in a resin called binder resin having a binding function. In the layered type function-separated photoreceptor, provided is a layered type photosensitive layer that comprises a layered type structure of a charge generating layer with a charge generating substance dispersed in a binder resin and a charge transporting layer with a charge transporting substance dispersed in a binder resin.

As the charge generating substance for use in the function-separated photoreceptor, investigated are various materials such as phthalocyanine pigments, squarylium dyes, azo pigments, perylene pigments, polycyclic quinone pigments, cyanine dyes, squaric acid dyes, and pyrylium salt dyes, and various materials having good light resistance and good charge generating capability have been proposed.

Further, various compounds have been known as the charge transporting substance, for example, pyrazoline compounds (for example, refer to Japanese Examined Patent Publication JP-B2 52-4188 (1977)), hydrazone compounds (for example, refer to Japanese Unexamined Patent Publication JP-A 54-150128 (1979), Japanese Examined Patent Publication JP-B2 55-42380 (1980), and Japanese Unexamined Patent Publication JP-A 55-52063 (1980)), triphenylamine compounds (for example, refer to Japanese Examined Patent Publication JP-B2 58-32372 (1983), and Japanese Unexamined Patent Publications JP-A 2-190862 (1990)), and stilbene compounds (for example, Japanese Unexamined Patent Publications JP-A 54-151955 (1979) and JP-A 58-198043 (1983)). In recent years, a compound having a central parent nucleus of a condensed polycyclic hydrocarbon-base substance has been developed, the compound which includes, for example, a pyrene derivative, a naphthalene derivative, and a terphenyl derivative (for example, refer to Japanese Unexamined Patent Publication JP-A 7-48324 (1995)).

The charge transporting substances must satisfy the following requirements:

(1) they are stable to light and heat, (2) they are stable to active substances such as ozone, nitrogen oxide (chemical formula: $NO_x$) and nitric acid generated by corona discharging in charging the photoreceptor, (3) they have high charge transporting ability, (4) they have high compatibility with an organic solvent and a binder resin, and (5) they can be manufactured easily and inexpensively. However, while the above-stated charge transporting substances can satisfy a portion of the demands but have not yet satisfy all of the demands at high level.

Further, as to characteristics of the photoreceptor, the photoreceptors are required to exhibit good sensitivity even when used in low-temperature environments, and moreover are required to be excellent in environment stability with the characteristics thereof changing in a small range depending on the fluctuation of the ambient environment such as temperature and humidity. However, the charge transporting substances having such characteristics have not yet been obtained.

Further, in recent years, of the above-stated demands, particularly high charge transporting ability has been required for the charge transporting substance. For example, higher sensitivity has been demanded as the photoreceptor characteristics for responding to the requirements of reduction in size and increase in speed of image forming operation to electrophotographic apparatuses such as copying machines and printers, and the charge transporting ability of the charge transporting substance has been demanded to improve as means for attaining higher sensitivity of the photoreceptor.

Further, in the high-speed electrophotographic process, since the time from exposure to the development is short, a photoreceptor of excellent light responsiveness has been required. In a case where the light responsiveness of the photoreceptor is poor, that is, the decaying speed of the surface potential of the photosensitive layer by exposure is slow, the residual potential rises, with the result that the photoreceptor is used repetitively in a state where the surface potential is not decayed sufficiently. Therefore, the surface charges at a portion to be erased are not sufficiently erased by exposure, thereby causing deterioration of the picture quality such as lowering of the image density in an early stage. In the function-separated photoreceptor, the charges generated from the charge generating substance upon light absorption are transported by the charge transporting substance to the surface of the photosensitive layer so that the surface charges of the photosensitive layer at a portion irradiated with a light are eliminated. Therefore, the light responsiveness depends on the charge transporting ability of the charge transporting substance. Accordingly, high charge transporting ability is required for the charge transporting substance also from a viewpoint of attaining a photoreceptor which has high light responsiveness and is capable of forming high quality images even in a high-speed electrophotographic process.

Further, the high durability of electrophotographic apparatus is also demanded. In order to attain the high durability, it is necessary that an electrophotographic photoreceptor has excellent durability and can operate stably for a long period of time. The durability of the photoreceptor is largely influenced by the printing resistance of the outermost layer of the photoreceptor. In a case where a photoreceptor is used being mounted on an electrophotographic apparatus, the outermost layer of the photoreceptor is inevitably scraped at a portion thereof by a contact member such as a cleaning blade or a charge roller. In a case where a scraped amount of the outermost layer of the photoreceptor through the sliding contact, namely an amount of film reduction is large, the electric charge-holding ability of the photoreceptor is lowered, and there arises the problem of the deterioration in image quality.

Accordingly, it is demanded for the outermost layer of a photoreceptor to be not readily scraped by the above-stated contact member, that is, to have high printing resistance.

In a case where the charge transporting layer forms the outermost layer of a photoreceptor, as the method of improving the printing resistance of the outermost layer of the photoreceptor, raising the binder resin content has been considered. However, in the case of raising the binder resin content, accordingly the charge transporting substance contained in the charge transporting layer is correspondingly lowered, and this poses the problem that the charge transporting capability of charge transporting layer is lowered and the responsiveness of photoreceptor to light is reduced. Further, from the poor compatibility of a charge transporting substance with a binder resin, the binder resin crystallizes during the preparation of film, and this also consequently poses the problem of causing image defects. Therefore, it has been difficult to realize the photoreceptors not only having good electric properties such as responsibility but also having good durability.

For the purpose of solving the above-mentioned problem, as the charge transporting substance excelling both in charge transporting ability and in compatibility with binder resin, the enamine compounds having enamine structure containing nitrogen atom substituted by different substituents are proposed (refer to Japanese Unexamined Patent Publication JP-A 2004-334125). However, in order to more certainly prevent image defects from being generated, further improvement in the compatibility with the binder resin is also demanded for the enamine compounds disclosed in JP-A 2004-334125.

For the purpose of solving the above-mentioned problem of electrographic photoreceptor, there has been an attempt of lowering the contents of a charge transporting substance by means of giving charge transporting function to a binder resin, and the development has been progressed for the binder resin containing a constituent unit having charge transporting function, that is, so called a photoconductive polymeric material. The specific examples include polycarbonate resin with triarylamine structure in a main chain or a side chain (for example, refer to Japanese Unexamined Patent Publications JP-A 3-221522 (1991), JP-A 4-11627 (1992), JP-A 6-295077 (1994), JP-A 7-258399 (1995) and JP-A 8-62864(1996)); and polyether resin with triarylamine structure in a main chain (for example, refer to Japanese Unexamined Patent Publication JP-A 8-176293 (1996)). These resins are synthesized by homopolymerization or copolymerization of monomers, using as the monomer the compounds having both triarylamine structure and hydroxyl group (for example, refer to Japanese Unexamined Patent Publications JP-A 7-228557 (1995), JP-A 9-194442 (1997), JP-A 2000-136169 and JP-A 2002-249472). However, triarylamine compounds disclosed in, for example, JP-A 7-228557 (1995), JP-A 9-194442 (1997), JP-A 2000-136169) and JP-A 2002-249472, have unsatisfactory charge transporting function, and the resins obtained by polymerization of these triarylamine compounds, which has thus triphenylamine structure, as disclosed in, for example, JP-A 3-221522 (1990), JP-A 4-11627 (1991), JP-A 6-295077 (1994), JP-A 7-258399 (1995), JP-A 8-62864 (1996) and JP-A 8-176293 (1996), have not yet satisfy at high level the demands with regard to charge transporting function and mechanical strength.

For the purpose of solving the above-mentioned problem of the photoconductive polymeric material, bishydroxy-substituted-enamine compounds (hereinafter referred to also as "-bis-hydroxyenamine compound") that have both enamine structure and two hydroxyl groups, have been proposed as the compounds being useful not only for a raw material compound of polymeric material but also for charge transporting substance by itself (refer to Japanese Unexamined Patent Publications JP-A 2004-269377).

Further, as another means to realize the high durability of photoreceptor, covering the photosensitive layer with a surface protective layer formed of resins or the like is practiced. In the case that the photoreceptor is equipped with a surface protective layer, since the surface protective layer forms the outermost layer, the surface protective layer is demanded to have excellent charge transporting function and excellent wear resistance. As the surface protective layer satisfying above-mentioned demands, the surface protective layer formed of the siloxane type resins containing the structure unit having charge transporting function has been proposed (refer to Japanese Unexamined Patent Publication JP-A 2000-242019).

The bis-hydroxyenamine compounds disclosed in JP-A 2004-269377 have, because of the nitrogen atoms contained in the enamine skeleton, which have the identical substituent groups, a high-symmetry molecule-structure which easily leads crystallization. This consequently poses such problems of poor solubility in solvents and poor compatibility with binder resins. Therefore, for example, in the case of using a bis-hydroxyenamine compound as a charge transporting substance in a charge transporting layer, a part of the compound remains undissolved in the coating solution for forming the layer, and consequently the undissolved part of the compound resides as crystalline in the charge transporting layer, bringing about such bad influences as the formation of image defects and the like. Further, the raw material compounds used for preparing the bis-hydroxyenamine compounds disclosed in JP-A 2004-269377, and an intermediate product generated in the manufacturing process are also easily crystallized, resulting in poor solubility in solvents, and this poses another problem that the reaction does not proceed smoothly. Further, in the case of preparing a polymeric material by using the compounds disclosed in JP-A 2004-269377, there arises the problem that the reaction does not proceed smoothly because of the poor solubility of the compounds in solvents.

From the studies of the inventors, it was found that the solubility of bis-hydroxyenamine compounds disclosed in JP-A 2004-269377 (hereinafter referred to also as "symmetrical bis-hydroxyenamine compound") in solvents and the compatibility of the compounds with binder resins are higher when the substituent groups substituting for the carbon atoms contained in the enamine skeleton are comparably small groups such as a methyl group, than when the substituent groups are large groups such as an aryl group. Therefore, it is possible to solve, to a certain extent, the above-mentioned problems arisen from the poor solubility in solvents and the poor compatibility with binder resins of the compounds. However, in the case that the substituent group on the enamine moiety of the compounds is an alkyl group, on the contrary, the compounds have some drawbacks that the electric properties, especially hole transporting capability, are inferior to those when the substituent group is an aryl group. Consequently, it has been demanded to enhance the solubility of the compounds in solvents and the compatibility of the compounds with binder resins without deteriorating the electric properties such as the hole transporting capability.

Further, the surface protective layers disclosed in JP-A 2000-242019 have not sufficient charge transporting ability, therefore the surface protective layer being excellent both in charge transporting ability and in mechanical strength has not been realized. Further, as to the photoreceptors disclosed in JP-A 2000-242019, there is incompatibility between the charge transporting substances in charge transporting layers and the structure unit with charge transporting function built in the siloxane type resins forming the surface protective layers. This incompatibility will lead formation of a potential barrier at the interface between the surface protective layer and the charge transporting layer, resulting in the insufficiency of charge injection, and there also arises the problem of decreases in sensitivity and light responsiveness.

SUMMARY OF THE INVENTION

An object of the invention is to provide an organic photoconductive material that can realize an electrophotographic photoreceptor which is not only excellent in charge transporting ability but also excellent in solubility in a solvent and compatibility with a resin and which does not cause partial crystallization or the like at the time of forming a film and moreover, which is excellent in both electric properties and durability, and the organic photoconductive material that is useful also as a raw material compound for various types of functional materials, and also provide to an electrophotographic photoreceptor using the organic photoconductive material, and an image forming apparatus provided with the electrophotographic photoreceptor.

The invention provides an asymmetric bis-hydroxyenamine compound represented by the following general formula (1) (hereinafter referred to also as "asymmetric bis-hydroxyenamine compound (1)"):

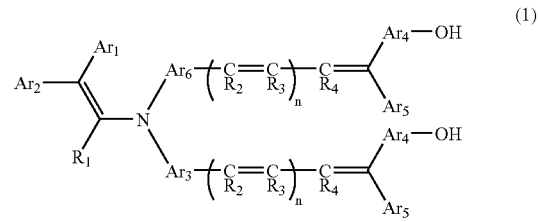

wherein $Ar_1$ and $Ar_2$ each may be the same or different, and each represent an aryl group which may have a substituent or a heterocyclic group which may have a substituent; $Ar_3$ represents an arylene group which may have a substituent or a divalent heterocyclic group which may have a substituent; two $Ar_4$s each may be the same or different, and each represent an arylene group which may have a substituent or a divalent heterocyclic group which may have a substituent; two $Ar_5$s each may be the same or different, and each represent a hydrogen atom, an aryl group which may have a substituent, a heterocyclic group which may have a substituent, an aralkyl group which may have a substituent, or an alkyl group which may have a substituent; $Ar_6$ represents an arylene group which may have a substituent or a divalent heterocyclic group which may have a substituent; $R_1$ represents a hydrogen atom or an alkyl group which may have a substituent; 2n number of $R_2$s and $R_3$s and two $R_4$s each may be the same or different, and each represent a hydrogen atom, an alkyl group which may have a substituent, an aryl group which may have a substituent, a heterocyclic group which may have a substituent, or an aralkyl group which may have a substituent; two pieces of "n"s may be the same or different, and each represent an integer of from 0 to 3; and $Ar_3$ and $Ar_6$ are not be same with each other.

Further, in the invention, it is preferable that the asymmetric bis-hydroxyenamine compound represented by the general formula (1) is an asymmetric bis-hydroxyenamine compound represented by the following general formula (2) (hereinafter, referred to also as "asymmetric bis-hydroxyenamine compound (2)"):

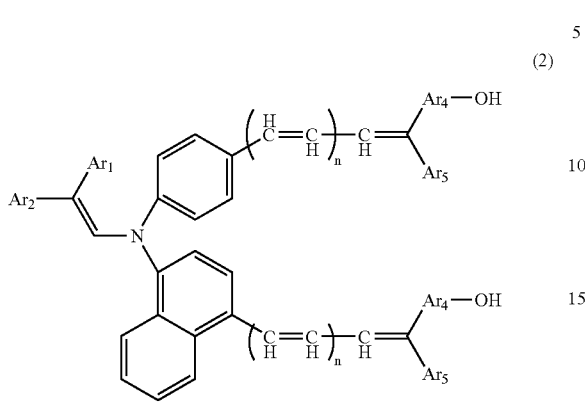

(2)

wherein $Ar_1$, $Ar_2$, $Ar_4$, $Ar_5$, and n are identical to those described above, respectively.

Further, in the invention, it is preferable that the asymmetric bis-hydroxyenamine compound represented by the general formula (1) is an asymmetric bis-hydroxyenamine compound represented by the following general formula (3) (hereinafter, referred to also as "asymmetric bis-hydroxyenamine compound (3)"):

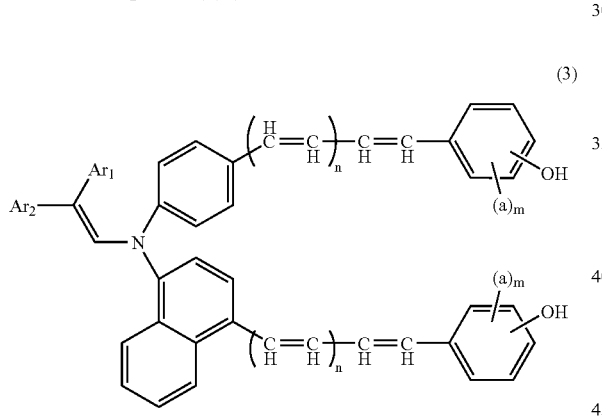

(3)

wherein $Ar_1$, $Ar_2$, and n are identical to those described above, respectively; 2m pieces of "a"s may be the same or different, and each represent an alkyl group which may have a substituent, an alkoxy group which may have a substituent, a dialkylamino group which may have a substituent, an aryl group which may have a substituent, a halogen atom, or a hydrogen atom; 2m pieces of "a"s may form monovalent condensed ring groups together with respective hydroxyphenyl groups to which the 2m pieces of "a"s are bonded; and two pieces of "m"s may be the same or different, and each represent an integer of from 1 to 4.

Further, in the invention, it is preferable that the asymmetric bis-hydroxyenamine compound represented by the general formula (1) is an asymmetric bis-hydroxyenamine compound represented by the following general formula (4) (hereinafter, referred to also as "asymmetric bis-hydroxyenamine compound (4)"):

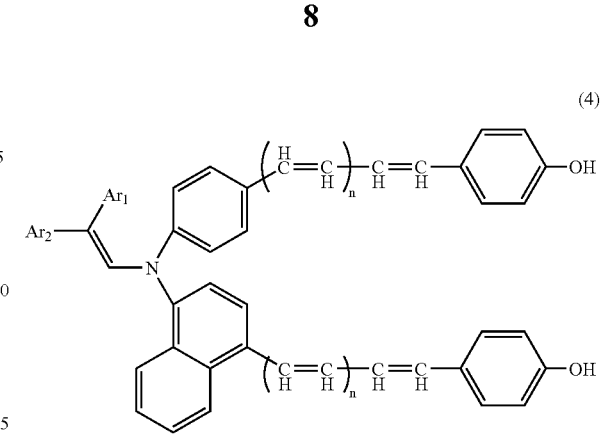

(4)

wherein $Ar_1$, $Ar_2$, and n are identical to those described above, respectively.

Further, in the invention, it is preferable that the asymmetric bis-hydroxyenamine compound represented by the general formula (1) is an asymmetric bis-hydroxyenamine compound represented by the following general formula (5) (hereinafter, referred to also as "asymmetric bis-hydroxyenamine compound (5)"):

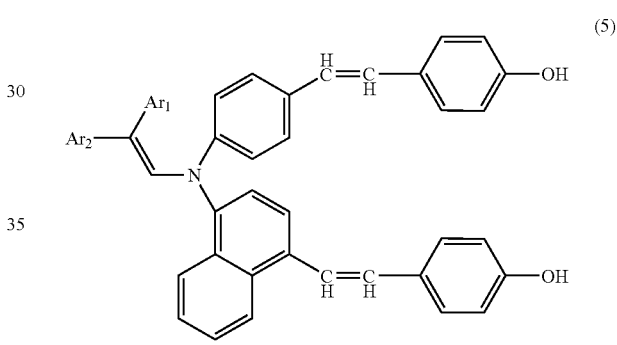

(5)

wherein $Ar_1$, and $Ar_2$ are identical to those described above, respectively.

Further, the invention provides an electrophotographic photoreceptor comprising:
a conductive substrate; and
a photosensitive layer provided on the conductive substrate, containing the asymmetric bis-hydroxyenamine compound mentioned above.

Further, the invention provides an electrophotographic photoreceptor comprising:
a conductive substrate;
a photosensitive layer provided on the conductive substrate; and
a surface protective layer provided on the conductive substrate, containing the asymmetric bis-hydroxyenamine compound mentioned above.

Further, the invention provides an image forming apparatus comprising:
the electrophotographic photoreceptor mentioned above;
charging means for charging the electrophotographic photoreceptor;
exposure means for exposing the charged electrophotographic photoreceptor to light; and
developing means for developing an electrostatic latent image formed by the exposure.

According to the invention, the asymmetric bis-hydroxyenamine compound (1) represented by the general formula (1) is provided. Since the asymmetric bis-hydroxyenamine compound according to the invention is not only excellent in a charge transporting function, particularly in a hole transporting function, but also excellent in solubility in a solvent and compatibility with a resin, it is useful as an organic photoconductive material and is advantageous as a charge transporting substance of devices such as an electrostatic recording device, a sensor device or an EL device of an electrophotographic photoreceptor or the like. For example, by allowing the asymmetric bis-hydroxyenamine compound according to the invention to be contained in the photosensitive layer or the surface protective layer of the electrophotographic photoreceptor, the electrophotographic photoreceptor which is not only favorable in electric properties such as chargeability, sensitivity, and light responsiveness but also excellent in durability and environment stability can be realized. Further, since the asymmetric bis-hydroxyenamine compound according to the invention is excellent in solubility in a solvent and compatibility with a binder resin, the asymmetric bis-hydroxyenamine compound is uniformly dispersed in the photosensitive layer or the surface protective layer without being crystallized therein. By using such electrophotographic photoreceptor as described above, an image of high quality being free of an image defect such as a black spot can stably be formed in various types of environments. Still further, even when the electrophotographic photoreceptor according to the invention is used in a high-speed electrophotographic process, the image of high quality can be provided by virtue of excellent light responsiveness of the electrophotographic photoreceptor. Even still further, the asymmetric bis-hydroxyenamine compound according to the invention is useful as a polymeric material such as a raw material compound of a carbonate resin, a polyether resin, a polyester resin or a polyurethane resin and, and by using the asymmetric bis-hydroxyenamine compound according to the invention as a monomer, a photoconductive polymeric material having an excellent charge transporting function can easily be obtained.

Further, according to the invention, when stability, that is, scarce decomposition or quality change as a chemical substance, easiness of obtaining a raw material, easiness and high yield of production, production cost and the like are taken into consideration, among the compounds represented as the asymmetric bis-hydroxyenamine compound (1), preferable is the asymmetric bis-hydroxyenamine compound (2), more preferable is the asymmetric bis-hydroxyenamine compound (3), still more preferable is the asymmetric bis-hydroxyenamine compound (4), and particularly preferable is the asymmetric bis-hydroxyenamine compound (5).

Further, according to the invention, the electrophotographic photoreceptor in which the asymmetric bis-hydroxyenamine compound according to the invention is contained in the photosensitive layer, is provided. The electrophotographic photoreceptor is excellent in electric properties such as sensitivity and responsiveness and durability, and does not contain a crystallized portion which causes an image defect in the photosensitive layer. By using such electrophotographic photoreceptor as described above, the image of high quality being free of the image defect such as the black spot can stably be formed.

Further, according to the invention, the electrophotographic photoreceptor in which the asymmetric bis-hydroxyenamine compound according to the invention is contained in the surface protective layer, is provided. Since the asymmetric bis-hydroxyenamine compound is uniformly dispersed in the photosensitive layer or the surface protective layer without being crystallized therein, the charge transporting function can fully be exerted. Therefore, the electrophotographic photoreceptor according to the invention is excellent not only in mechanical strength but also in electric properties such as sensitivity and responsiveness. By using such electrophotographic photoreceptor as described above, even when the electrophotographic photoreceptor is repeatedly used for a long period of time, the image of high quality being free of the image defect such as the black spot can be formed.

Further, according to the invention, the image forming apparatus is provided with the electrophotographic photoreceptor according to the invention. Since the electrophotographic photoreceptor according to the invention contains the asymmetric bis-hydroxyenamine compound according to the invention in the photosensitive layer or the surface protective layer, the electrophotographic photoreceptor is excellent in electric properties such as chargeability, sensitivity and light responsiveness, and durability. Still further, the asymmetric bis-hydroxyenamine compound according to the invention is uniformly dispersed in the photosensitive layer or the surface protective layer of the electrophotographic photoreceptor without being crystallized therein. Therefore, in the image forming apparatus according to the invention, the image of high quality being free of the image defect such as the black spot can stably be formed for a long period of time in various types of environments. Further, since the electrophotographic photoreceptor according to the invention is excellent in light responsiveness and can provide the image of high quality even in the high-speed electrophotographic process, an image forming speed can be increased in the image forming apparatus according to the invention.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
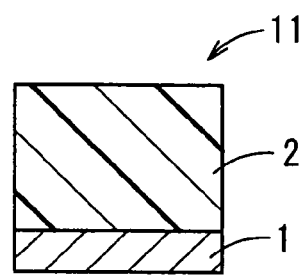
FIG. 1 is a cross sectional view schematically showing the main part of a single layer type electrophotographic photoreceptor according to another embodiment of the invention.

Now referring to the drawings, preferred embodiments of the invention are described below.

The asymmetrical bis-hydroxyenamine compound of the invention is an asymmetrical bis-hydroxyenamine compound represented by the following general formula (1), that is, an asymmetrical bis-hydroxyenamine compound (1). Of the asymmetrical bis-hydroxyenamine compounds (1), from the viewpoint of easiness in procuring or synthesizing a raw material and furthermore a low raw-material cost, from the viewpoint of chemical stability of the compounds, from the viewpoint of easiness in procuring and synthesizing of the compounds themselves, from the viewpoint of high synthesis yield, and from the viewpoint of a low production cost, preferable is the asymmetrical bis-hydroxyenamine compound (2) represented by the following general formula (2), more preferable is the asymmetrical bis-hydroxyenamine compound (3) represented by the following general formula (3); still more preferable is the asymmetrical bis-hydroxyenamine compound (4) represented by the following general formula (4), and particularly preferable is the asymmetrical bis-hydroxyenamine compound (5) represented by the following general formula (5).

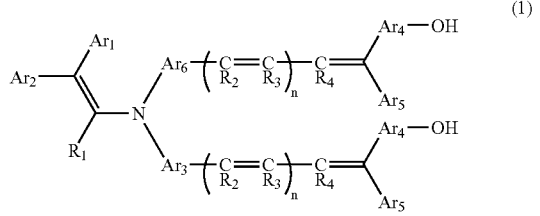

wherein $Ar_1$ and $Ar_2$ each may be the same or different, and each represent an aryl group which may have a substituent or a heterocyclic group which may have a substituent; $Ar_3$ represents an arylene group which may have a substituent or a divalent heterocyclic group which may have a substituent; two $Ar_4$s may be the same or different, and each represent an arylene group which may have a substituent or a divalent heterocyclic group which may have a substituent; two $Ar_5$s may be the same or different, and each represent a hydrogen atom, an aryl group which may have a substituent, a heterocyclic group which may have a substituent, an aralkyl group which may have a substituent, or an alkyl group which may have a substituent; $Ar_6$ represents an arylene group which may have a substituent or a divalent heterocyclic group which may have a substituent; $R_1$ represents a hydrogen atom or an alkyl group which may have a substituent; 2n number of $R_2$s and $R_3$s and two $R_4$s may be the same or different, and each represent a hydrogen atom, an alkyl group which may have a substituent, an aryl group which may have a substituent, a heterocyclic group which may have a substituent, or an aralkyl group which may have a substituent; two pieces of "n"s may be the same or different, and each represent an integer of from 0 to 3; and $Ar_3$ and $Ar_6$ should not be the same.

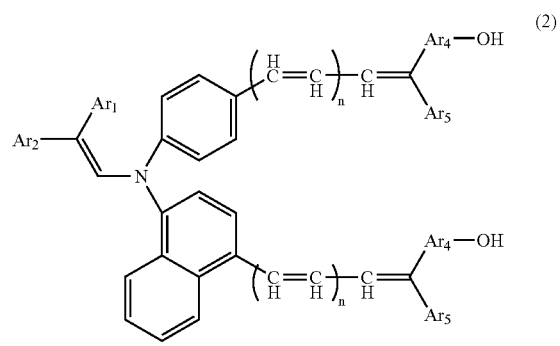

wherein $Ar_1$, $Ar_2$, $Ar_4$, $Ar_5$, and n are identical to those described above, respectively.

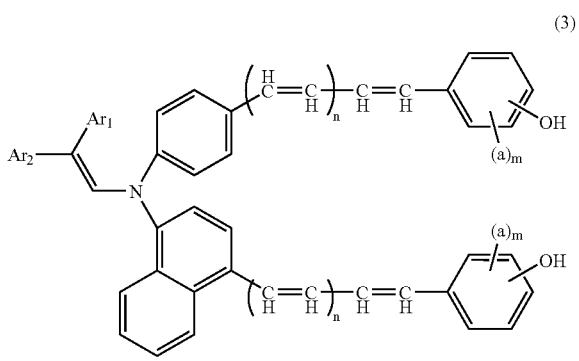

wherein $Ar_1$, $Ar_2$, and n are identical to those described above, respectively; 2m pieces of "a"s may be the same or different, and each represent an alkyl group which may have a substituent, an alkoxy group which may have a substituent, a dialkylamino group which may have a substituent, an aryl group which may have a substituent, a halogen atom, or a hydrogen atom; 2m pieces of "a"s may form monovalent condensed ring groups together with respective hydroxyphenyl groups to which the 2m pieces of "a"s are bonded; and two pieces of "m"s may be the same or different, and each represent an integer of from 1 to 4.

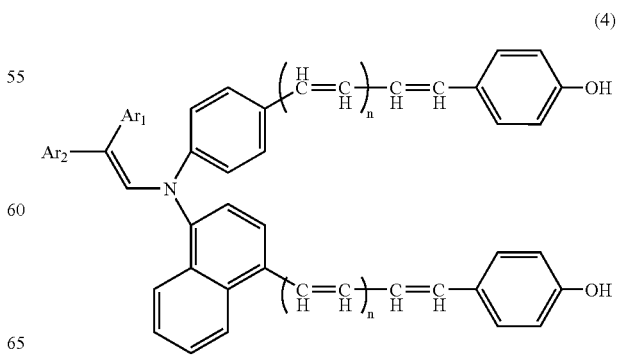

wherein Ar₁, Ar₂, and n are identical to those described above, respectively.

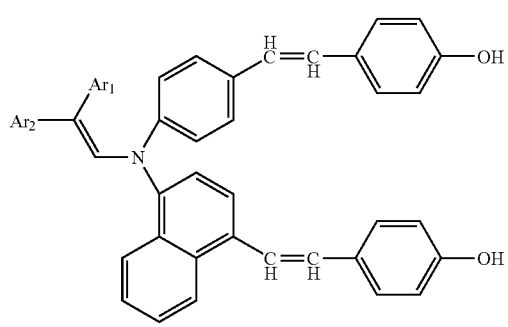

(5)

wherein Ar₁, and Ar₂ are identical to those described above, respectively.

In the general formulas (1)-(5), Ar₁ and Ar₂ represent an aryl group which may have a substituent. Examples of the aryl group include phenyl, tolyl, methoxyphenyl, naphthyl, and biphenylyl, each of which has a substituent selected from a C1-4 alkyl group and a C1-4 alkoxy groups. Among these aryl groups, preferable are phenyl, tolyl, methoxyphenyl, and naphthyl.

Further, in the general formulas (1)-(5), Ar₁ and Ar₂ also represent a heterocyclic group which may have a C1-4 alkyl group as a substituent. Examples of the heterocyclic group include furyl, thienyl, thiazolyl, benzofuryl and N-methylindolyl.

The group represented by Ar₃ and Ar₆ in the general formula (1), and furthermore represented by Ar₄ in the general formulas (1) and (2) is an arylene group which may have a substituent. Examples of the arylene group include p-phenylene, m-phenylene, methyl-p-phenylene, methoxy-p-phenylene, 1,4-naphthylene, pyrenylene, biphenylilene, phenoxyphenylene, and phenylthiophenylene, which may have a substituent selected from a C1-4 alkyl group, a C1-4 alkoxy group, a phenoxy group, and a phenylthio group. Among these arylene groups, preferable are p-phenylene, m-phenylene, methyl-p-phenylene, methoxy-p-phenylene, and 1,4-naphthylene, and particularly preferable are p-phenylene and 1,4-naphthylene. Further, in the general formula (1), Ar₃ and Ar₆ also represent a divalent heterocyclic group which may have a substituent. Examples of the divalent heterocyclic group include 1,4-furandiyl, 1,4-thiophenediyl, 1,4-thiazolediyl, 2,5-benzofurandiyl, 2,5-benzothiophenediyl, N-methylindole-2,5-diyl, 2,5-benzothiazolediyl, 2,5-benzoxazolediyl, and N-ethylcarbazole-3,6-diyl. Particularly preferable is the case where one of Ar₃ and Ar₆ is p-phenylene and the other is 1,4-naphthylene, namely the case of using the asymmetrical bis-hydroxyenamine compound represented by the general formula (2) because of a low price of raw materials or easiness in synthesizing the bis-hydroxyenamine compound. Further, more preferable is the case where Ar₄ is a phenylene group, namely the case of using the asymmetrical bis-hydroxyenamine compound represented by the general formula (3) because of a lower price of raw materials, easiness in synthesizing the bis-hydroxyenamine compound, and a high yield thereof. And still more preferable is the case where Ar₄ is a p-phenylene group, namely the case of using the asymmetrical bis-hydroxyenamine compound represented by the general formula (4) or (5).

In the general formulas (1) and (2), Ar₅ represents an aryl group which may have a substituent. Example of the aryl group include phenyl, tolyl, methoxyphenyl, naphthyl, pyrenyl, biphenylyl, phenoxyphenyl, p-(phenylthio)phenyl, and p-styrylphenyl, which has a substituent selected from C1-4 alkyl, C1-4 alkoxy, phenoxy, phenylthio and styryl. Among these aryl groups, preferable are phenyl, methoxyphenyl and naphthyl. Further, in the general formulas (1) and (2), Ar₅ also represents a heterocyclic group which may have a substituent. Examples of the divalent heterocyclic group include furyl, thienyl, thiazolyl, benzofuryl, benzothiophenyl, N-methylindolyl, benzothiazolyl, benzoxazoyl and N-ethylcarbazolyl, which may have a C1-4 alkyl group as a substituent. Further, in the general formulas (1) and (2), Ar₅ also represents an aralkyl group which may have a substituent. Examples of the aralkyl group include benzyl, p-methoxybenzyl, and 1-naphthylmethyl, which may have a C1-4 alkoxy group as a substituent. Further, in the general formulas (1) and (2), Ar₅ also represents an alkyl group which may have a substituent. Examples of the alkyl group include such a linear or branching C1-4 alkyl group as methyl, 2-thienylmethyl, ethyl, trifluoromethyl, fluoromethyl, isopropyl, and tert-butyl, which may have a substituent selected from a halogen atom and a thienyl group. The alkyl group may also include a cycloalkyl group such as cyclohexyl and cyclopentyl.

In the general formula (1), R₁ represents an alkyl group which may have a substituent. Examples of the alkyl group include such a linear or branching C1-4 alkyl group as methyl, ethyl, n-propyl, isopropyl, and trifluorometyl, which may have a halogen atom as a substituent.

In the general formula (1), the group represented by R₂, R₃, and R₄ is an alkyl group which may have a substituent. Examples of the alkyl group include such a linear or branching C1-4 alkyl group as methyl, ethyl, n-propyl, isopropyl, trifluorometyl, and 2-thienylmethyl, which may have a substituent selected from a halogen atom and a thienyl group. Further, in the general formula (1), R₂, R₃, and R₄ also represent an aryl group which may have a substituent. Examples of the aryl group include phenyl, tolyl, methoxyphenyl, and naphthyl, which may have a substituent selected from a C1-4 alkyl group and C1-4 alkoxy group. Among these aryl groups, preferable are phenyl and naphthyl. Further, in the general formula (1), R₂, R₃, and R₄ also represent a heterocyclic group which may have a substituent. Examples of the heterocyclic group include furiy, thienyl, and thiazolyl. Further, in the general formula (1), R₂, R₃, and R₄ also represent an aralkyl group which may have a substituent. Examples of the aralkyl group include benzyl and p-methoxybenzyl, which may have a C1-4 alkoxy group as a substituent.

In the general formula (3), the group represented by (a) is an alkyl group which may have a substituent. Examples of the alkyl group include such a linear or branching C1-3 alkyl group as methyl, ethyl, n-propyl, isopropyl, trifluorometyl and 2-thienylmethyl, which may have a substituent selected from a halogen atom and a thienyl group, Further, in the general formula (3), (a) also represents an alkoxy group which may have a substituent. Examples of the alkoxyl group include such a linear or branching C1-3 alkoxyl group as methoxyl, ethoxy, n-propoxy and isopropoxy. Further, in the general formula (3), (a) also represents a dialkylamino group which may have a substituent. Examples of the dialkylamino group include a C2-8 dialkylamino group such as dimethylamino, diethylamino and diisopropylamino. Further, in the general formula (3), (a) also represents an aryl group which may have a substituent. Examples of the aryl group include phenyl, tolyl, methoxyphenyl and naphthyl, which may have a substituent selected from a C1-4 alkyl group and a C1-4 alkoxy group. Among these aryl groups, preferable are phenyl and naphthyl. Examples of the halogen atom include fluorine, chlorine, bromine, and iodine. Among these halogen atoms, preferable are fluorine and chlorine.

In the general formula (3), 2m pieces of "a"s represent a monovalent condensed ring group that may be formed together with respective hydroxyphenyl groups to which the 2m pieces of "a"s are bonded. Examples of the monovalent condensed ring group include 2,3-methylenedioxy-4-hydroxyphenyl.

An asymmetrical bis-hydroxyenamine compound (1) is prepared, for example, according to the following reaction process schemes, by preparing an ether compound of bis-hydroxyenamine ((12a) or (12b)) and deprotecting a hydroxyl group by removing a protecting group represented by $R_7$.

which may have a substituent. Examples of the alkyl group include such a linear or branching C1-4 alkyl group as methyl, ethyl, n-propyl, isopropyl, trifluoromethyl, 2-thienylmethyl, which may have a substituent selected from a halogen atom and a thienyl group. Further, in the reaction process scheme, $R_5$, $R_6$ and $R_7$ represent an aryl group which may have a substituent. Examples of the aryl group include phenyl, tolyl, methoxyphenyl and naphthyl, which may have a substituent selected from a C1-4 alkyl group and a C1-4 alkoxy group. Among these aryl groups, preferable are phenyl and naphthyl.

Further, in the reaction process scheme, $R_5$ and $R_7$ represent a heterocyclic group which may have a substituent. Examples of the heterocyclic group include furyl, thienyl, and thiazolyl. Further, in the reaction process scheme, $R_5$ and $R_7$

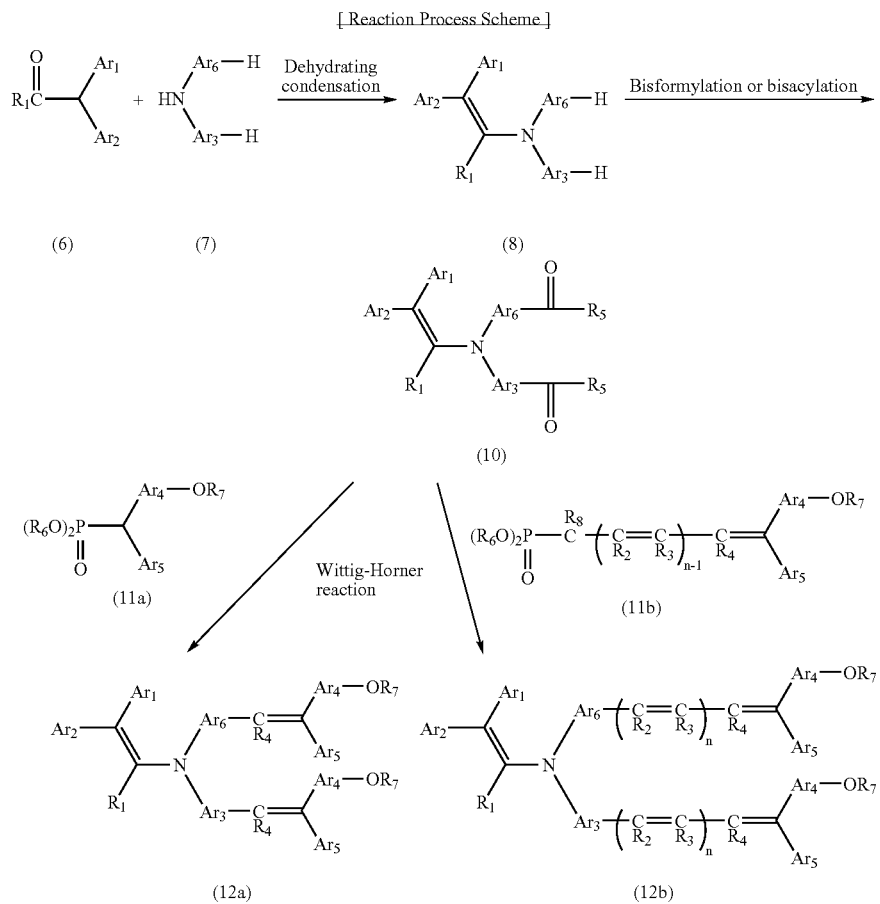

wherein $Ar_1$, $Ar_2$, $Ar_3$, $Ar_4$, $Ar_5$, $Ar_6$, $R_1$, $R_2$, $R_3$, $R_4$ and n are identical to those described above; two $R_5$s each may be the same or different, and each represent a hydrogen atom, an alkyl group which may have a substituent, an aryl group which may have a substituent, a heterocyclic group which may have a substituent, or an aralkyl group which may have a substituent; two $R_6$s each may be the same or different, and each represent alkyl group which may have a substituent or an aryl group which may have a substituent; $R_7$ may represent an aryl group which may have a substituent, a heterocyclic group which may have a substituent, or an aralkyl group which may have a substituent.

In the reaction process scheme, $R_5$, $R_6$ and $R_7$ represent an alkyl group which may have a substituent or an aryl group also represent an aralkyl group which may have a substituent. Examples of the aralkyl group include benzyl and p-methoxybenzyl, which have in an alkyl portion thereof a linear or branching C1-3 alkylene group, and may have a C1-4 alkoxy group as substituent.

Each reaction represented in the reaction process scheme is, for example, effected as follows:

The dehydrating condensation of a carbonyl compound represented in the general formula (6) (hereinafter referred to also as "carbonyl compound (6)") and a secondary amine compound represented in the general formula (7) (hereinafter referred to also as "secondary amine compound (7)") is effected in the presence of acid catalyst in an appropriate solvent under heat. The ratio of the to-be-used carbonyl compound (6) to the to-be-used secondary amine compound (7) is not particularly limited, and taking the efficiency of reaction into consideration, equimolar use thereof is preferable. Specific examples of usable acid catalyst are, p-toluenesulfonic acid, camphorsulfonic acid, and pyridinium-p-toluenesulfonic acid. The amount of the acid catalyst to be added is, for example, based on 1 molar equivalent of the carbonyl compound (6), preferably in the range of from 0.001 to 0.1 molar equivalents, more preferably from 0.002 to 0.04 molar equivalents, even more preferably from 0.005 to 0.02 molar equivalents (hereinafter the term may be simply referred to also as "equivalent weight"). The reaction solvent is not particularly limited, in so far as the solvent is inert to the reaction and can dissolve or disperse two kinds of the raw material compounds and the acid catalyst. Specific examples of usable solvent include aromatic hydrocarbons such as toluene and xylene, halogenated aromatic hydrocarbons such as chlorobenzene, lower alcohols such as butanol, and ethers such as diethyleneglycoldimethylether. The reaction temperature may be appropriately selected depending on the type and amount of the raw material compounds and the acid catalyst. Water is sometimes formed as a by-product during the reaction and interferes with the reaction being in progress, and therefore the by-product water is preferably removed from the reaction system through azeotropic distillation with the solvent used. As a result, the enamine intermediate (hereinafter referred to also as "enamine intermediate (8)") represented by the general formula (8) is prepared.

The bisformylation of enamine intermediate (8) is, for example, effected by Vilsmeier reaction. The reaction is specifically effected for example as follows: The enamine intermediate (8) and a Vilsmeier reagent are heated under stirring, and then the product is hydrolyzed. Any Vilsmeier reagent conventionally known may be utilized. Examples of such a reagent include a Vilsmeier reagent which can be obtained by the reaction of phosphorus oxychloride with one or more formamides in an appropriate solvent. Herein, specific examples of usable solvent include N,N-dimethylformamide and 1,2-dichloroethane. The N,N-dimethylformamide can be utilized as one of the formamides applied to the reaction with phosphorus oxychloride. Formamides include not only N,N-dimethylformamide, but also N-methyl-N-phenylformamide, and N,N-diphenylformamide. The ratio of the to-be-used Vilsmeier reagent to the to-be-used enamine intermediate (8) is not particularly limited, and taking the reaction efficiency into consideration, for example, the amount of the Vilsmeier reagent is preferably in the range of from 2.0 to 2.3 equivalent weights based on 1 equivalent weight of the enamine intermediate (8). The reaction is, for example, effected under stirring under heat at 60 to 110° C., and brought to an end after 2-8 hours or so.

After the reaction is terminated, the reaction mixture is hydrolyzed with an aqueous alkali solution and then, as a precitate of an intended compound, obtained is a compound (hereinafter referred to also as "bis-carbonyl intermediate (10a)"), which has two $R_5$s of hydrogen atoms, among the bis-carbonyl intermediates represented by the general formula (10) (hereinafter referred to also as "bis-carbonyl intermediate (10)"). The usable alkali herein include commonly-used alkali agent such as sodium hydroxide and potassium hydroxid. The alkali agent is used in the form of an aqueous solution, and the concentration thereof may be preferably 1-8 N. The amount of the alkali applied to the reaction mixture is not particularly limited, and it is necessary, for example, that a 1-8 N aqueous alkali solution is added until the precipitation of the intended compound is completed.

Further, the bisacylation of the enamine intermediate (8) is, for example, effected by Friedel-Craft reaction. Specifically, the reaction is effected by reacting the enamine intermediate (8) and a Friedel-Craft reagent and then hydrolyzing the reaction product. A reaction solvent may be utilized without particular limitations in so far as the solvent is inert to the reaction and can dissolve or disperse the enamine intermediate (8) and Friedel-Craft reagent. The solvent includes, for example, 1,2-dichloroethane. The Friedel-Craft reagent, for example, may be obtained by the reaction of the halogenated-acyl compound (hereinafter referred to also as "halogenated-acyl compound (9)") represented by the following general formula:

$$X\text{—}CO\text{—}R_5 \qquad (9)$$

(wherein $R_5$ is identical to that described above) with a Lewis acid. Herein, the Lewis acid includes alminium chloride, tin chloride, and zinc chloride. The amount of Lewis acid is not particularly limited, and taking the reaction efficiency into consideration, for example, the amount of the Lewis acid is preferably in the range of from 3.2 to 3.8 equivalent weights based on 2.5 to 2.8 equivalent weights of the halogenated-acyl compound (9). Further, the ratio of the to-be-used enamine intermediate (8) to the to-be-used Friedel-Craft reagent is not particularly limited, and taking the reaction efficiency into consideration, the amount of the Friedel-Craft reagent is preferably in the range of from 2.0 to 2.3 equivalent weights based on the amount of 1 equivalent weight of the enamine intermediate (8). The reaction is, for example, effected under stirring under heat at −40 to 80° C., and brought to an end after 2-8 hours or so.

After the reaction is terminated, the reaction mixture is hydrolyzed with an aqueous alkali solution to obtain the compound (hereinafter referred to also as "bis-carbonyl intermediate (10b)"), which has the two $R_5$s of groups other than hydrogen atoms, among the bis-carbonyl intermediates (10). The hydrolysis with alkali may be effected in a similar way to that of the hydrolysis for obtaining the bis-carbonyl intermediate (10b)

Further, the bis-carbonyl intermediate (10) is utilized in the Wittig-Horner reaction, and through this reaction of the bis-carbonyl intermediate (10) with a Wittig reagent, obtained is an ether compound (hereinafter referred to also as "ether compound (12a) or ether compound (12b)") represented by the general formula (12a) or (12b), the ether compound which is to be the precursor of the asymmetrical bis-hydroxyenamine compound (1).

Herein, the Wittig reagent includes a compound represented by the general formula (11a) or (11b) (hereinafter referred to also as "Wittig reagent (11a) or Wittig reagent (11b)"). Further, in the Wittig reagent (11a) or Wittig reagent (11b), the hydroxyl group which further substitutes for the substituent group represented by $Ar_4$, is protected by the substituent group represented by $R_7$.

An ether compound (12a) is obtained by the reaction of the bis-carbonyl intermediate (10) with the Wittig reagent (11a), and through replacing the protecting group of the ether compound (12a), which is represented by $R_7$, obtained is a compound (hereinafter referred to also as "asymmetrical bis-hydroxyenamine compound (1a)"), which has (n) of 0 in the general formula (1) of the asymmetrical bis-hydroxyenamine compound.

Further, an ether compound (12b) is obtained by the reaction of the bis-carbonyl intermediate (10) with the Wittig reagent (11b), and through replacing the protecting group of the ether compound (12b), which is represented by $R_7$, obtained is a compound (hereinafter referred to also as "asymmetrical bis-hydroxyenamine compound (1b)"), which has (n) of from 1 to 3 in the general formula (1) of the asymmetrical bis-hydroxyenamine compound.

The Wittig-Horner reaction for the bis-carbonyl intermediate (10) may be effected by the conventionally known procedure. For example, the reaction of the bis-carbonyl intermediate (10) with the Wittig reagent (11a) or Wittig reagent (11b) may be effected in an appropriate solvent in the presence of such a catalyst as metal alkoxide base. A reaction solvent may be utilized without particular limitations, in so far as the solvent is inert to the reaction and can dissolve or disperse a reaction substrate and a catalyst. The solvent includes aromatic hydrocarbons such as toluene and xylene, ethers such as diethylether, tetrahydrofuran, and ethyleneglycoldimethylether, amides such as N,N-dimethylformamide, and sulfoxides such as dimethlsulfoxide. The solvent may be used alone, or two or more of the solvents may be used in combination. Further, the amount of the solvent is not particularly limited, and may be appropriately selected depending on various conditions such as the amount of the reaction substrate, the reaction temperature and the reaction time, so that the reaction may proceed smoothly. The usable metal alkoxide base includes a conventionally known alkoxide base such as potassium-t-butoxide, sodium ethoxide, and sodium methoxide. The alkali metal alkoxide base may be used alone, or two or more of the alkali metal alkoxide bases may be used in combination at the same time. The amounts of the reaction substrate and catalyst are not particularly limited, and can vary widely according to the reaction condition, however, in order to conduct the reaction smoothly, based on 1 equivalent weight of the bis-carbonyl intermediate (10), a preferable amount of the Wittig reagent (11a) or Wittig reagent (11b) is in the range of from 2.0 to 2.3 equivalent weights, and a preferable amount of the catalyst is in the range of from 2.0 to 2.5 equivalent weights. This reaction is effected, for example, under stirring at room temperature or under heat at 30 to 60° C., and brought to an end after 2-8 hours or so. By this reaction, the ether compound (12a) or the ether compound (12b) is obtained.

The deprotection of the ether compound (12a) or ether compound (12b) is effected by a conventional known procedure. For example, the deprotection may be effected by reacting the ether compound (12a) or ether compound (12b) with a deprotection agent in an appropriate solvent. The usable deprotection agent includes a hydrogen halide such as hydrogen bromide and hydrogen iodide, and an aluminum halide such as aluminum chloride and aluminum bromide. The deprotection agent also includes boron tribromide and sodium ethanethiolate. The deprotection agent may be used alone, or two or more of the deprotection agents may be used in combination at the same time. The amount of deprotection agent is not particularly limited, however, in order to conduct the reaction smoothly and in order to isolate and purify an intended compound easily, based on 1 equivalent weight of the ether compound (12a) or ether compound (12b), the amount of the deprotection agent is in the range of from 2.0 to 8.0 equivalent weights, and preferably from 2.0 to 3.0 equivalent weights, and more preferably from 2.2 to 2.6 equivalent weights. A reaction solvent may be utilized without particular limitations, in so far as the solvent is inert to the reaction and can dissolve the reaction substrate without the decomposition thereof. The usable solvent includes aromatic hydrocarbons such as benzene and nitrobenzene, halogenated aromatic hydrocarbons such as chlorobenzene, formamides such as N,N-dimethylformamide, and acetic anhydride and dichloromethane. The solvent may be appropriately selected depending on a kind of deprotection agent. For example, in a case of using hydrogen halide, acetic anhydride is preferable. In a case of using aluminum halogenide, aromatic hydrocarbons and halogenated aromatic hydrocarbons are preferable. In a case of using boron trifluorid, dichloromethane is preferable. In a case of using sodium ethanethiolate, formamides are preferable. The amount of solvent is not particularly limited, and can vary widely depending on various conditions such as the kinds, amounts, reaction temperature, etc. of the reaction substrate and deprotection agent. This deprotection reaction may be effected, for example, under cooling or in a reflux state of the solvent being in a range from a room temperature to a boiling point, and brought to an end after 0.5-24 hours. Further, the reaction temperature may be selected so that the reaction may proceed smoothly. By this reaction, the asymmetrical bis-hydroxyenamine compound (1) is obtained.

Thus obtained asymmetrical bis-hydroxyenamine compound may easily isolated and purified from the reaction mixture after the reaction by commonly used purifying procedures such as extraction, chromatograpy, centrifugation, recrystallization and washing.

Specific examples of the asymmetrical bis-hydroxyenamine compound (1) are shown in Table 1 to Table 9.

TABLE 1

| Compound No. | $Ar^1$ | $Ar^2$ | $R^1$ | $N-Ar^3$ | $N-Ar^6$ | n |
|---|---|---|---|---|---|---|
| 1 | 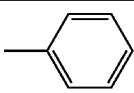 | 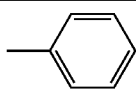 | H | 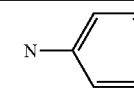 | 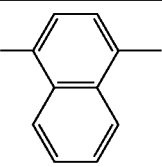 | 0 |
| 2 | 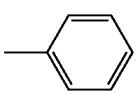 | 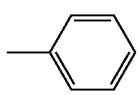 | H | 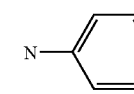 | 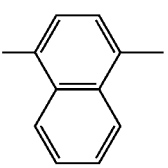 | 1 |

TABLE 1-continued

| # | (structure) | (structure) | | (structure) | |
|---|---|---|---|---|---|
| 3 | methylphenyl | methylphenyl | H | N-phenyl-N'-(4-methylnaphthyl)-p-phenylenediamine | 2 |
| 4 | 4-methoxyphenyl | 4-methoxyphenyl | H | N-phenyl-N'-(4-methylnaphthyl)-p-phenylenediamine | 0 |
| 5 | 2-fluorophenyl | 2-fluorophenyl | H | N-phenyl-N'-(4-methylnaphthyl)-p-phenylenediamine | 0 |
| 6 | 5,6,7,8-tetrahydronaphthyl | 5,6,7,8-tetrahydronaphthyl | H | N-phenyl-N'-(4-methylnaphthyl)-p-phenylenediamine | 0 |
| 7 | 4-methoxyphenyl | phenyl | H | N-phenyl-N'-(4-methylnaphthyl)-p-phenylenediamine | 0 |
| 8 | 1-naphthyl | 1-naphthyl | H | N-phenyl-N'-(4-methylnaphthyl)-p-phenylenediamine | 0 |
| 9 | 2-benzothiazolyl | 2-benzothiazolyl | H | N-phenyl-N'-(4-methylnaphthyl)-p-phenylenediamine | 0 |

| Compound No. | R² | R³ | R⁴ | Ar⁴—OH | Ar⁵ |
|---|---|---|---|---|---|
| 1 | — | — | H | 4-hydroxyphenyl | H |
| 2 | H | H | H | 4-hydroxyphenyl | H |
| 3 | H | H | H | 4-hydroxyphenyl | H |

TABLE 1-continued
| | | | | |
|---|---|---|---|---|
| 4 | — — | H | 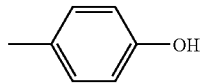 | H |
| 5 | — — | H | 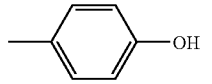 | H |
| 6 | — — | H | 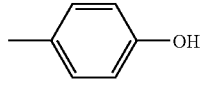 | H |
| 7 | — — | H | 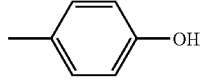 | H |
| 8 | — — | H | 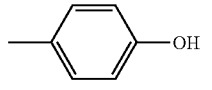 | H |
| 9 | — — | H | 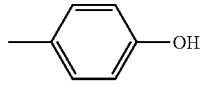 | H |
TABLE 2
| Compound No. | Ar¹ | Ar² | R¹ | N—Ar³ | N—Ar⁶ | n |
|---|---|---|---|---|---|---|
| 10 | 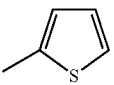 | 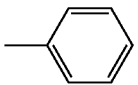 | H | 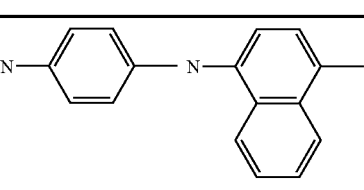 | 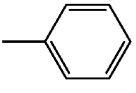 | 0 |
| 11 | 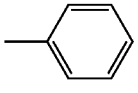 | 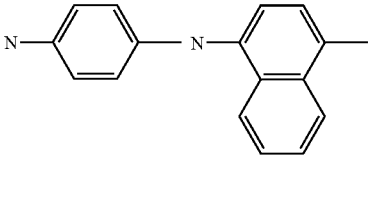 | H | 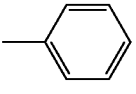 | 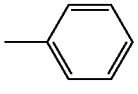 | 0 |
| 12 | 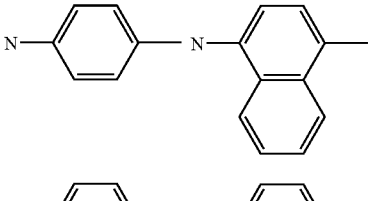 | 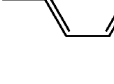 | H | 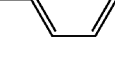 | 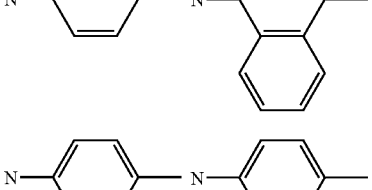 | 1 |
| 13 | 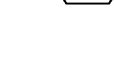 |  | H | 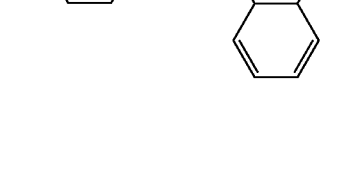 | | 2 |
| 14 | | | H | | | 0 |

TABLE 2-continued

| | | | | | |
|---|---|---|---|---|---|
| 15 | —C6H5 | —C6H5 | H | N—C6H4—N-(naphthyl)— | 0 |
| 16 | —C6H5 | —C6H5 | H | N—C6H4—N-(naphthyl)— | 0 |
| 17 | —C6H5 | —C6H5 | H | N—C6H4—N-(naphthyl)— | 1 |
| 18 | —C6H5 | —C6H5 | H | N—C6H4—N-(naphthyl)— | 1 |

| Compound No. | $R^2$ | $R^3$ | $R^4$ | $Ar^4$—OH | $Ar^5$ |
|---|---|---|---|---|---|
| 10 | — | — | H | —C6H4—OH (para) | H |
| 11 | — | — | H | —C6H4—OH (para) | —CH3 |
| 12 | H | H | H | —C6H3(CH3)—OH | —CH3 |
| 13 | H | H | H | —C6H4—OH (para) | —CH3 |
| 14 | — | — | H | —C6H4—OH (para) | —C6H5 |
| 15 | — | — | —C2H5 | —C6H4—OH (para) | H |
| 16 | — | — | —C6H4—CH(CH3)2 | —C6H4—OH (para) | H |
| 17 | H | H | —CH3 | —C6H4—OH (para) | H |

TABLE 2-continued
| 18 | H | H | 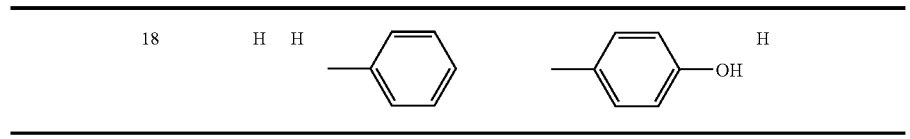 | |
|---|---|---|---|---|
TABLE 3
| Compound No. | Ar¹ | Ar² | R¹ | N—Ar³ | N—Ar⁶ | n |
|---|---|---|---|---|---|---|
| 19 | 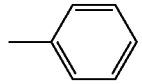 |  | H | 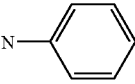 | 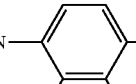 | 0 |
| 20 | 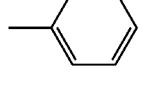 | 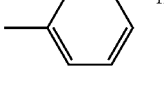 | H | 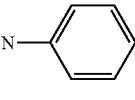 | 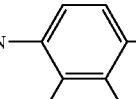 | 0 |
| 21 | 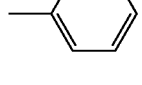 | 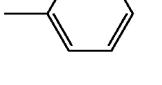 | H | 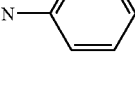 | 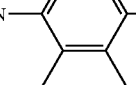 | 1 |
| 22 | 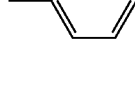 | 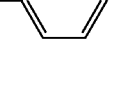 | H | 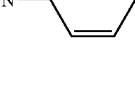 | 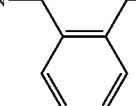 | 1 |
| 23 | 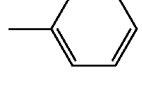 |  | H | 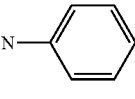 | 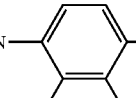 | 2 |
| 24 | 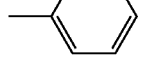 | 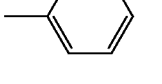 | H | 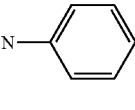 | 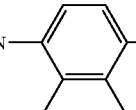 | 1 |
| 25 | 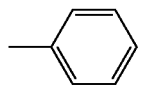 |  | H | 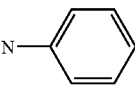 | 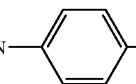 | 1 |

TABLE 3-continued

| 26 | -C6H4-C6H5 (biphenyl) | H | N-(p-phenylene)-N-(4-methylnaphthalen-1-yl) | 1 |

| Compound No. | R² | R³ | R⁴ | Ar⁴—OH | Ar⁵ |
|---|---|---|---|---|---|
| 19 | — | — | —CH₃ | 4-hydroxyphenyl | —CH₃ |
| 20 | — | — | phenyl | 4-hydroxyphenyl | —CH₃ |
| 21 | H | H | —CH₃ | 2,4,5-trimethyl-6-hydroxyphenyl (H₃C, CH₃, CH₃ substituted hydroxyphenyl) | —CH₃ |
| 22 | H | H | phenyl | 4-hydroxyphenyl | —CH₃ |
| 23 | H | H | —CH₃ | 4-hydroxyphenyl | —CH₃ |
| 24 | H | H | —CH₃ | 4-hydroxyphenyl | phenyl |
| 25 | H | H | —CH₃ | 4-hydroxyphenyl | H |
| 26 | H | H | phenyl | 4-hydroxyphenyl | —CH₃ |

TABLE 4

| Compound No. | Ar¹ | Ar² | R¹ | N—Ar³ | N—Ar⁶ | n |
|---|---|---|---|---|---|---|
| 27 | phenyl | phenyl | H | N-(p-phenylene) | N-(4-methylnaphthalen-1-yl) | 1 |
| 28 | phenyl | phenyl | H | N-(p-phenylene) | N-(4-methylnaphthalen-1-yl) | 1 |

TABLE 4-continued
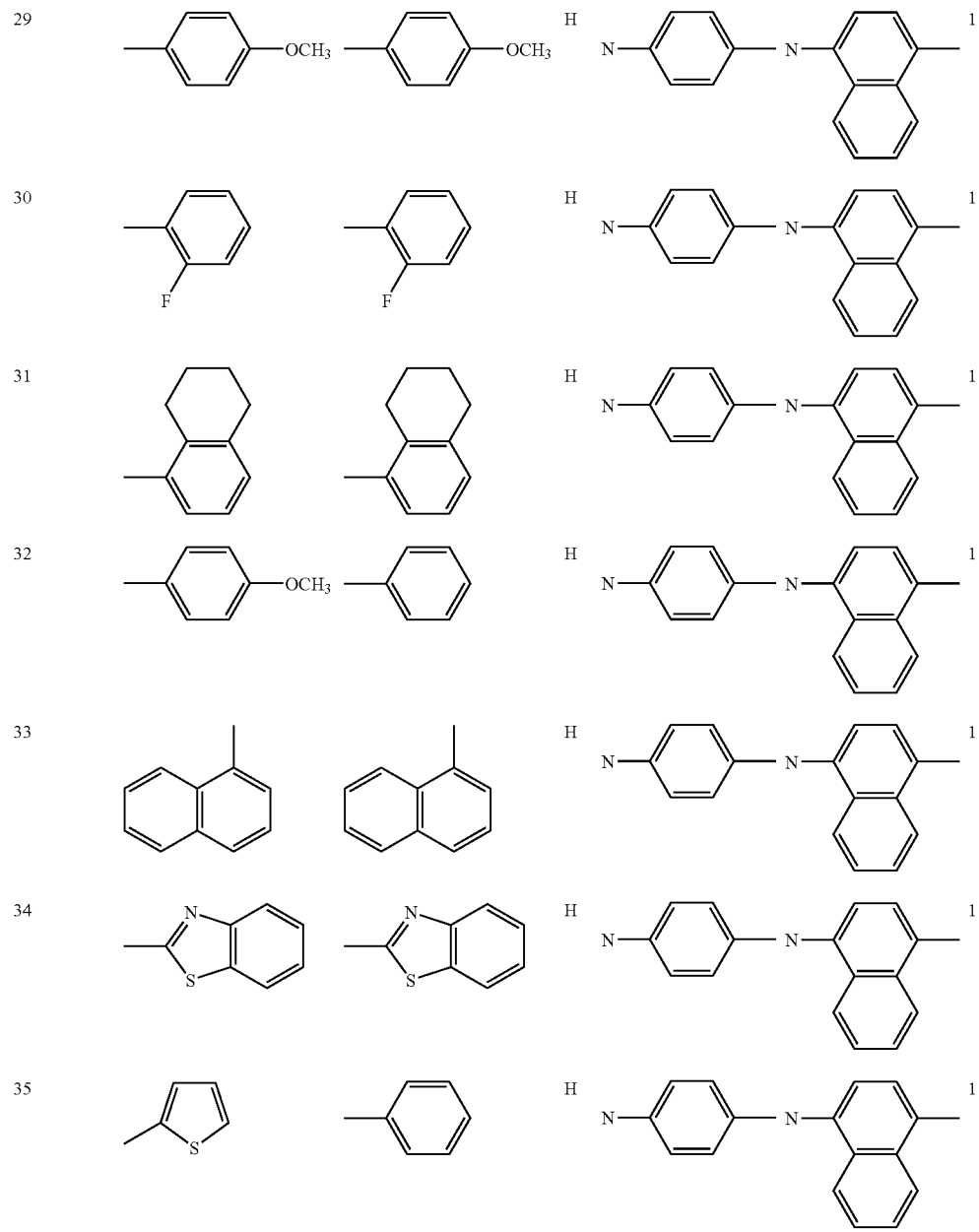
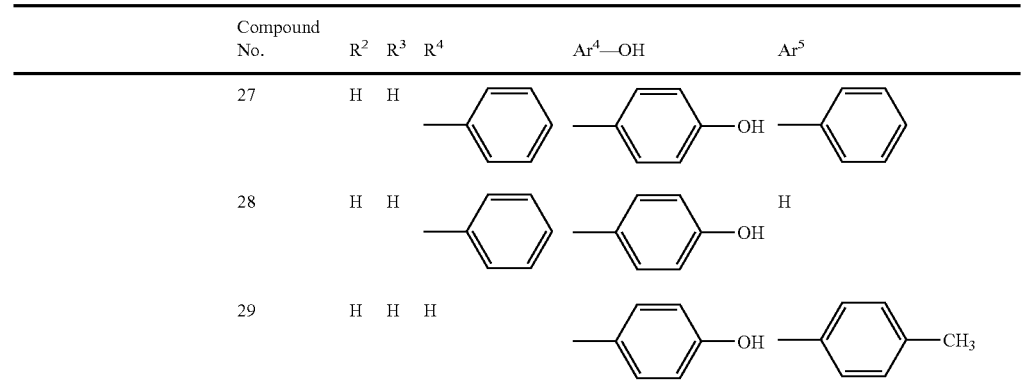

TABLE 4-continued

| No. | | | | Structure | |
|---|---|---|---|---|---|
| 30 | H | H | H | 4-hydroxyphenyl | H |
| 31 | H | H | H | 4-hydroxyphenyl | 4-N(CH$_3$)$_2$-phenyl |
| 32 | H | H | H | 4-hydroxyphenyl | phenyl |
| 33 | H | H | H | 4-hydroxyphenyl | phenyl |
| 34 | H | H | —C$_2$H$_4$ | 4-hydroxyphenyl | H |
| 35 | H | H | phenyl | 4-hydroxyphenyl | H |

TABLE 5

| Compound No. | Ar$^1$ | Ar$^2$ | R$^1$ | N—Ar$^3$ | N—Ar$^6$ | n |
|---|---|---|---|---|---|---|
| 36 | phenyl | phenyl | H | N-(1,4-phenylene) | N-(4-naphthyl) | 1 |
| 37 | phenyl | phenyl | H | N-(1,4-phenylene) | N-(4-naphthyl) | 1 |
| 38 | phenyl | phenyl | H | N-(1,4-phenylene) | N-(4-naphthyl) | 1 |
| 39 | phenyl | phenyl | H | N-(1,4-phenylene) | N-(4-naphthyl) | 1 |
| 40 | phenyl | phenyl | H | N-(1,4-phenylene) | N-(4-naphthyl) | 1 |

TABLE 5-continued

| 41 | ![phenyl] | ![phenyl] | H | ![N-phenyl] | ![2-methyl-naphthyl-N] | 0 |
| 42 | ![phenyl] | ![phenyl] | H | ![N-phenyl] | ![3-fluoro-naphthyl-N] | 0 |

| Compound No. | $R^2$ | $R^3$ | $R^4$ | $Ar^4$—OH | $AR^5$ |
|---|---|---|---|---|---|
| 36 | H | —CH$_2$F | H | ![4-hydroxyphenyl] | H |
| 37 | H | ![2-thienyl] | H | ![4-hydroxyphenyl] | H |
| 38 | H | ![benzyl] | H | ![4-hydroxyphenyl] | H |
| 39 | —CH$_3$ | H | H | ![4-hydroxyphenyl] | H |
| 40 | H | —CH$_3$ | ![phenyl] | ![4-hydroxyphenyl] | H |
| 41 | — | — | H | ![4-hydroxyphenyl] | H |
| 42 | — | — | H | ![4-hydroxyphenyl] | H |

TABLE 6

| Compound No. | $Ar^1$ | $Ar^2$ | $R^1$ | N—$Ar^3$ | N—$Ar^6$ | n |
|---|---|---|---|---|---|---|
| 43 | ![phenyl] | ![phenyl] | H | ![N-phenyl-N] | ![N-methyl-methoxynaphthyl] | 0 |

TABLE 6-continued

| Compound No. | R² | R³ | R⁴ | Ar⁴—OH | Ar⁵ |
|---|---|---|---|---|---|
| 43 | — | — | H | 4-hydroxyphenyl | —CH₃ |
| 44 | — | — | H | 4-hydroxyphenyl | 4-(phenylthio)phenyl |
| 45 | — | — | H | 4-hydroxyphenyl | —CH₃ |
| 46 | — | — | H | 4-hydroxyphenyl | —CH₃ |
| 47 | — | — | H | 4-hydroxyphenyl | H |
| 48 | — | — | H | 4-hydroxyphenyl | 3-ethylphenyl (with CH₃) |

TABLE 7
| Compound No. | Ar¹ | Ar² | R¹ | N—Ar³ | N—Ar⁶ | n |
|---|---|---|---|---|---|---|
| 49 |  |  | H |  |  | 0 |
| 50 |  |  | H |  |  | 1 |
| 51 |  |  | H |  |  | 1 |
| 52 |  |  | H |  |  | 1 |
| 53 |  |  | H |  |  | 1 |
| 54 |  |  | H |  |  | 1 |
| 55 |  |  | H |  |  | 1 |
| Compound No. | R² | R³ | R⁴ | Ar⁴—OH | Ar⁵ |
|---|---|---|---|---|---|
| 49 | — | — | H |  |  |
| 50 | H | H | H |  |  |
| 51 | H | H | H |  | H |
| 52 | H | H | H |  | H |
| 53 | H | H | H |  | H |

TABLE 7-continued

| 54 | H | H | iso-C₃H₇ | ![p-cresol/OH structure] | H |
| 55 | H | H | H | ![p-cresol/OH structure] | H |

TABLE 8

| Compound No. | Ar¹ | Ar² | R¹ | N—Ar³ | N—Ar⁶ | n |
|---|---|---|---|---|---|---|
| 56 | 4-methylphenyl | 4-methylphenyl | H | 4-methylphenyl | 9-ethyl-carbazol-3-yl with methyl | 1 |
| 57 | 4-methoxyphenyl | 4-methoxyphenyl | H | 4-methylphenyl | 4-methylnaphthalen-1-yl | 0 |
| 58 | 2-fluorophenyl | 2-fluorophenyl | H | 4-methylphenyl | 4-methylnaphthalen-1-yl | 0 |
| 59 | 5,6,7,8-tetrahydronaphthalen-1-yl | 5,6,7,8-tetrahydronaphthalen-1-yl | H | 4-methylphenyl | 4-methylnaphthalen-1-yl | 0 |
| 60 | 4-methoxyphenyl | phenyl | H | 4-methylphenyl | 4-methylnaphthalen-1-yl | 0 |
| 61 | naphthalen-1-yl | naphthalen-1-yl | H | 5-methylbenzofuran-2-yl | 4-methylnaphthalen-1-yl | 0 |

TABLE 8-continued

| | | | Compound No. | R² | R³ | R⁴ | Ar⁴—OH | Ar⁵ |
|---|---|---|---|---|---|---|---|---|
| 62 | (2-benzothiazolyl) | (2-benzothiazolyl) | H | (N-p-tolyl) | (N-4-methylnaphth-1-yl) | 0 | | |
| | | | 56 | H | H | n-C₄H₉ | 4-methylphenol | H |
| | | | 57 | — | — | H | 4-methylphenol | H |
| | | | 58 | — | — | H | 4-methylphenol | H |
| | | | 59 | — | — | H | 3,5-dimethyl-4-methylphenol | H |
| | | | 60 | — | — | H | 4-methylphenol | —CH₃ |
| | | | 61 | — | — | H | 4-methylphenol | —CH₃ |
| | | | 62 | — | — | H | 4-methylphenol | —CH₃ |

TABLE 9

| Compound No. | Ar¹ | Ar² | R¹ | N—Ar³ | N—Ar⁶ |
|---|---|---|---|---|---|
| 63 | 2-thienyl | phenyl | H | N-phenyl | N-(4-methylnaphth-1-yl) |
| 64 | phenyl | phenyl | —CH₃ | N-phenyl | N-(4-methylnaphth-1-yl) |

TABLE 9-continued

| 65 | 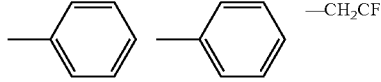 | 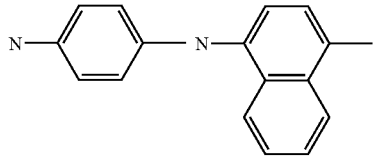 | —CH$_2$CF$_3$ | 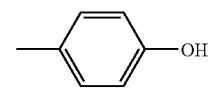 | |

| Compound No. | n | R$^2$ | R$^3$ | R$^4$ | Ar$^4$—OH | Ar$^5$ |
|---|---|---|---|---|---|---|
| 63 | 1 | H | H | H | 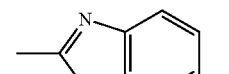 | H |
| 64 | 1 | H | H | H | 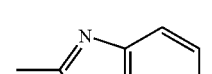 | H |
| 65 | 1 | H | H | H |  | H |

The asymmetrical bis-hydroxyenamine compound of the invention is useful for an organic photoconductive material, and especially useful for charge transporting substances in a photosensitive layer and in a surface protective layer of the electrophotographic photoreceptor that will be described hereinbelow. Further, the asymmetrical bis-hydroxyenamine compound of the invention has two hydroxyl groups, and is therefore useful also as a raw material compound of various polymeric materials, especially of the polymeric materials derived from the compounds having two hydroxyl groups. For example, by using the asymmetrical bis-hydroxyenamine compound of the invention as a monomer of polymeric material such as polycarbonate resin, polyether resin, polyester resin, and polyurethane resin, it is possible to obtain a photoconductive polymeric material which is excellent in charge transporting function and useful for a photoconductive polymeric material.

A polymeric material such as polycarbonate resin, polyether resin, polyester resin and polyurethane resin can be prepared by the same procedure as the preparation of each conventional resin, except that one or more asymmetrical bis-hydroxyenamine compounds of the invention are used as diols.

For example, a polycarbonate resin can be prepared in the same manner as the preparation of conventional polycarbonate resin except that one or more asymmetrical bis-hydroxyenamine compounds of the invention and one or more carbonate compounds are used as raw material compounds at the same time. Any carbonate compound that has been utilized for the preparation of the conventional polycarbonate resins can also be used. Examples of the carbonate compound include a halogenated carbonyl compound such as phosgene and bis(trichloromethyl)carbonate (another name: triphosgene), bisarylcarbonates such as bisphenylcarbonate, and halogenated formates such as bischloroformate. Examples of the halogenated formates includes the bishalogenated formates derived from the dihydroxy compound having two hyroxy groups. Examples of the dihydoxy compound used as the raw material of the bishalogenated formate include, for example, 4,4'-(1-methylethylidene)bisphenol, 4,4'-(1-methylethylidene)bis(2-methylphenol), 4,4'-cyclohexylidenebisphenol, and 4,4'-ethylidene bisphenol.

The copolymerization reaction of the asymmetrical bis-hydroxyenamine compounds of the invention with a carbonate compound can be effected by the conventionally known procedure. For example, in a case that a halogenated carbonyl compound is used as a carbonate compound, a polycarbonate resin is obtained through solution-polymerization or interfacial polymerization. Further, in a case that bisarylcarbonates are used as a carbonate compound, a polycarbonate resin is obtained through transesterification.

The asymmetrical bis-hydroxyenamine compound of the invention is excellent in solubility in solvents, and therefore dissolves easily in the solvent used in the polymerization process. Therefore, by using the asymmetrical bis-hydroxyenamine compound of the invention, the polymerization reaction can be effected smoothly, with the result that the above-mentioned polymeric materials being useful for photoconductive material can be obtained easily.

FIG. 1 to FIG. 8 are cross sectional views schematically showing the main part of an electrophotographic photoreceptor (hereinafter the term may be simply referred to also as "photoreceptors"). The electrophotographic photoreceptors 11 to 14 shown in FIG. 1 to FIG. 4 are each a single layer type electrophotographic photoreceptor characterized in that a photosensitive layer 2 is a single-layered photoreceptor 2 composed of only one layer. Further, the electrophotographic photoreceptors 15 to 18 shown in FIG. 5 to FIG. 8 are each a layered type electrophotographic photoreceptor (hereinafter the term may be referred to also as "function-separated electrophotographic photoreceptor") characterized in that a photosensitive layer 7 is a layered type photosensitive layer 7 (hereinafter the term may be referred to also as "function-separated photosensitive layer") composed of a charge generating layer 3 and a charge transporting layer 4.

The electrophotographic photoreceptor 11 shown in FIG. 1 comprises a conductive substrate (metal tube for electrophotographic photoreceptor) 1, and the photosensitive layer 2 formed on the conductive substrate 1.

Figure 2:
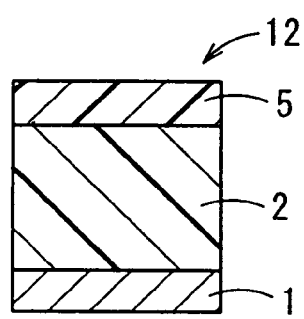
FIG. 2 is a cross sectional view schematically showing the main part of a single layer type electrophotographic photoreceptor according to another embodiment of the invention.

The electrophotographic photoreceptor 12 shown in FIG. 2 comprises the conductive substrate 1, the photosensitive layer 2 formed on the surface of conductive substrate 1, and a surface protective layer 5 formed on the surface of photosensitive layer 2.

Figure 3:
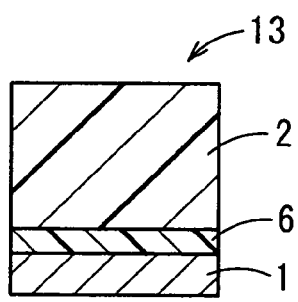
FIG. 3 is a cross sectional view schematically showing the main part of a single layer type electrophotographic photoreceptor according to another embodiment of the invention.

The electrophotographic photoreceptor 13 shown in FIG. 3 comprises the conductive substrate 1, the intermediate layer 6 formed on the surface of conductive substrate 1, and the photosensitive layer 2 formed on the intermediate layer 6.

Figure 4:
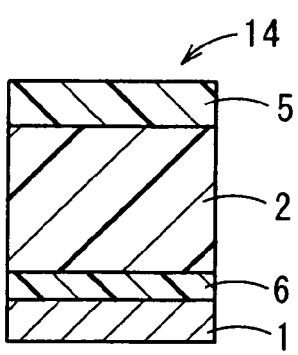
FIG. 4 is a cross sectional view schematically showing the main part of a single layer type electrophotographic photoreceptor according to another embodiment of the invention.

The electrophotographic photoreceptor 14 shown in FIG. 4 comprises the conductive substrate 1, the intermediate layer 6 formed on the surface of conductive substrate 1, the photosensitive layer 2 formed on the intermediate layer 6, and the surface protective layer 5 formed on the surface of photosensitive layer 2.

Figure 5:
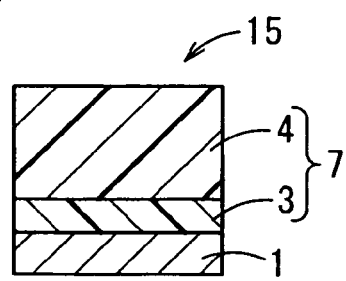
FIG. 5 is a cross sectional view schematically showing the main part of a layered type electrophotographic photoreceptor according to another embodiment of the invention.

The electrophotographic photoreceptor 15 shown in FIG. 5 comprises the conductive substrate 1, the charge generating layer 3 formed on the surface of conductive substrate 1, and the charge transporting layer 4 formed on the charge generating layer 3.

Figure 6:
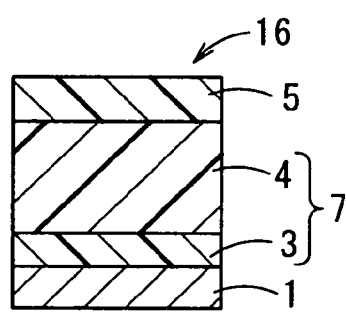
FIG. 6 is a cross sectional view schematically showing the main part of a layered type electrophotographic photoreceptor according to another embodiment of the invention.

The electrophotographic photoreceptor 16 shown in FIG. 6 contains the conductive substrate 1, the charge generating layer 3 formed on the surface of conductive substrate 1, the charge transporting layer 4 formed on the charge generating layer 3, and the surface protective layer 5 formed on the charge transporting layer 4.

Figure 7:
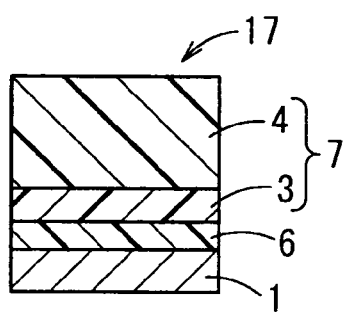
FIG. 7 is a cross sectional view schematically showing the main part of a layered type electrophotographic photoreceptor according to another embodiment of the invention.

The electrophotographic photoreceptor 17 shown in FIG. 7 comprises the conductive substrate 1, the intermediate layer 6 formed on the surface of conductive substrate 1, the charge generating layer 3 formed on the intermediate layer 6, and the charge transporting layer 4 formed on the charge generating layer 3.

Figure 8:
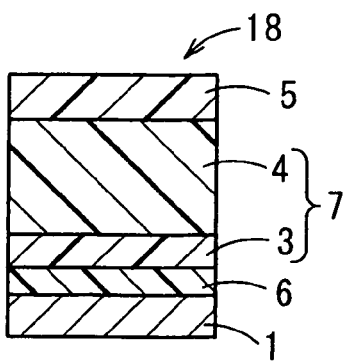
FIG. 8 is a cross sectional view schematically showing the main part of a layered type electrophotographic photoreceptor according to another embodiment of the invention.

The electrophotographic photoreceptor 18 shown in FIG. 8 comprises the conductive substrate 1, the intermediate layer 6 formed on the surface of conductive substrate 1, the charge generating layer 3 formed on the intermediate layer 6, the charge transporting layer 4 formed on the charge generating layer 3, and the surface protective layer 5 formed on the charge transporting layer 4.

Layers constituting the electrophotographic photoreceptors 11 to 18 in FIG. 1 to FIG. 8 are described below.

[Conductive Substrate]

A conductive substrate 1 is constituted by, for example, a metallic material such as aluminum, an aluminum alloy, copper, zinc, stainless steel, or titanium. Further, the conductive substrate 1 is not limited to these metallic materials, and it is possible to use a polymeric material such as polyethylene terephthalate, polyamide, polyester, polyoxymethylene or polystyrene; an article in which a metallic foil is laminated on a substrate surface containing hard paper or glass; an article in which a metallic material is vapor-deposited on the substrate surface; or an article in which a layer of a conductive compound such as a conductive polymer, tin oxide, or indium oxide is vapor-deposited or coated on the substrate surface. Although the conductive substrate 1 is illustrated in a sheet shape in each of the electrophotographic photoreceptors 11 to 18 shown in FIG. 1 to FIG. 8, the shape of the conductive substrate 1 is not limited thereto, and a columnar shape, a cylindrical shape, an endless belt shape or the like is permissible.

A surface of the conductive substrate 1 may optionally be subjected to an anodic oxide film treatment, a surface treatment by using a chemical or hot water, coloring treatment, or a diffuse reflection treatment by roughening the surface. The diffuse reflection treatment is particularly effective when the electrophotographic photoreceptor according to the invention is used in an electrophotographic process in which laser is used as an exposure light source. That is, in the electrophotographic process in which laser is used as the exposure light source, since a wavelength of laser light is aligned, the laser light reflected on the surface of the electrophotographic photoreceptor and the laser light reflected inside the electrophotographic photoreceptor are interfered with each other, to thereby sometimes generate an image defect in which an interference pattern appears in an image. By subjecting the surface of the conductive substrate 1 to the diffuse reflection treatment, the image defect to be caused by the interference of the laser light having the thus-aligned wavelength can be prevented.

[Single Layer Type Photosensitive Layer]

A photosensitive layer 2 which is a single layer type photosensitive layer is constituted by containing a charge generating substance, the asymmetric bis-hydroxyenamine compound according to the invention, and a binder resin. In the photosensitive layer 2, the asymmetric bis-hydroxyenamine compound according to the invention functions as a charge transporting substance. The photosensitive layer 2 may, optionally, contain any one of other charge transporting substances than the asymmetric bis-hydroxyenamine compound according to the invention, an additive such as an antioxidant, and the like.

The charge generating substance is a substance which generates charge by absorbing light. As for such charge generating substances, substances as ordinarily used in the art can be used. Examples thereof include organic pigments or dyes such as azo type pigments (such as a monoazo type pigment, a bisazo type pigment, and a trisazo type pigment), indigo type pigments (such as indigo and thioindigo), perylene type pigments (such as perylenimide and perylenic anhydride), polycyclic quinone type pigments (such as anthraquinone and pyrene quinone), phthalocyanine type pigments (such as a metallophthalocyanine and a non-metallophthalocyanine), squalium colorants, pyrilium salts, thiopyrilium salts, and triphenylmethane type colorants; and inorganic substances such as selenium and amorphous silicon. The charge generating substances may be each used alone, or two or more of the charge generating substances may be used in combination.

Among these charge generating substances, an X type non-metallophthalocyanine and a metallophthalocyanine are preferable, and oxotitanium phthalocyanine is more preferable. The X type non-metallophthalocyanine, the metallophthalocyanine and, particularly, the oxotitanium phthalocyanine have high charge generating efficiency and charge injection efficiency, with the result that these substances generate a large amount of charges by absorbing light and, then, efficiently inject the thus-generated charges into the asymmetric bis-hydroxyenamine compound according to the invention which is the charge transporting substance contained in the photosensitive layer 2 or photosensitive layer 7, without storing the charges inside molecules of these compounds. Therefore, the charges generated at the charge generating substances by absorbing the light are efficiently injected into the asymmetric bis-hydroxyenamine compound according to the invention which is used as the charge transporting substance and smoothly transported. This makes it possible to obtain the electrophotographic photoreceptor of high sensitivity and high resolution.

The charge generating substance may be used in combination with any one of a triphenylmethane type dye represented by methyl violet, crystal violet, night blue or Victoria blue, an acridine type dye represented by erythrosine, rhodamine B, rhodamine 3R, acridine orange or flapeocine, a thiazine type dye represented by methylene blue, or methylene green, an oxazine dye represented by Capri blue or Meldola's blue, and a sensitizing dye such as a cyanine dye, a styryl dye, a pyrylium salt dye, or a thiopyrylium salt dye.

As for the asymmetric bis-hydroxyenamine compound according to the invention to be used as the charge transporting substance, one or more compounds selected from the asymmetric bis-hydroxyenamine compounds (1) can be used.

Any one of other charge transporting substances than the asymmetric bis-hydroxyenamine compound according to the invention can be used, for example, for further enhancing the electric properties of the photosensitive layer 2. The charge transporting substance includes a hole transporting substance and the charge transporting substance. As for such hole transporting substances, substances as ordinarily used in the art can be used. Examples thereof include a carbazole derivative, a pyrene derivative, an oxazole derivative, an oxadiazole derivative, a thiazole derivative, a thiadiazole derivative, a triazole derivative, an imidazole derivative, an imidazolone derivative, an imidazolidine derivative, a bis-imidazolidine derivative, a styryl compound, a hydrazone compound, a polycyclic compound, an indole derivative, a pyrazoline derivative, an oxazolone derivative, a benzimidazole derivative, a quinazoline derivative, a benzofuran derivative, an acridine derivative, a phenazine derivative, an aminostilbene derivative, a triarylamine derivative, a triarylmethane derivative, a phenylene diamine derivative, a stilbene derivative, an enamine derivative, a benzidine derivative, a polymer having a group derived from these compounds in a main chain or a side chain (such as poly-N-vinylcarbazole, poly-1-vinylpyrene, ethylcarbazole-formaldehyde resin, triphenylmethane polymer, or poly-9-vinylanthracene), and polysilane. As for such charge transporting substances, substances as ordinarily used in the art can be used. Examples thereof include organic compounds such as a benzoquinone derivative, a tetracyanoethylene derivative, a tetracyanoquinodimethane derivative, a fluorenone derivative, a xanthone derivative, a phenanthrenequinone derivative, a phthalic anhydride derivative, and a diphenoquinone derivative; and inorganic materials such as amorphous silicon, amorphous selenium, tellurium, a selenium-tellurium alloy, cadmium sulfide, cadmium sulfide, zinc oxide, and zinc sulfide. The charge transporting substances may be each used alone, or two or more of the charge transporting substances may be used in combination.

The binder resin is used, for example, for enhancing the mechanical strength and durability of the photosensitive layer 2. As for the binder resin, a resin having a bonding property is used. As for the binder resin, a resin excellent in compatibility with the asymmetric bis-hydroxyenamine compound according to the invention is favorably used. Specific examples of such binder resins include vinyl type resins such as polymethylmethacrylate, polystyrene, and polyvinyl chloride; thermoplastic resins such as polycarbonate, polyester, polyester carbonate, polysulfone, polyallylate, polyamide, methacrylic resins, acrylic resins, polyether, polyacrylamide, and polyphenylene oxide; thermosetting resins such as phenoxy resins, epoxy resins, silicone resins, polyurethane, phenol resins; and partially cross-linked articles of these resins. Among these resins and articles, polystyrene, polycarbonate, polyallylate and polyphenylene oxide are particularly excellent in compatibility with the asymmetric bis-hydroxyenamine compound according to the invention and, also, excellent in electric insulation such that each of them has a volume resistance of $10^{13} \Omega$ or more and, further, excellent in film-forming properties and residual potential properties, resulting in favorable usability as a binder resin. Among these resins, polycarbonate can particularly favorably be used. The binder resins may be each used alone, or two or more of the binder resins may be used in combination.

A ratio of the to-be-used asymmetric bis-hydroxyenamine compound according to the invention to the to-be-used binder resin is not particularly limited and, in the photosensitive layer 2 and the charge transporting layer 4, the amount of the binder resin to be used is, based on 100 parts by weight of the asymmetric bis-hydroxyenamine compound according to the invention, in the range of from 50 parts by weight to 300 parts by weight. When the amount of the binder resin to be used is, based on 100 parts by weight of the asymmetric bis-hydroxyenamine compound according to the invention, less than 50 parts by weight, an abrasion amount becomes large and, then, there is a risk of inviting an insufficient durability. When the amount of the binder resin to be used is more than 300 parts by weight, there is a risk of reducing the sensitivity.

The antioxidant can reduce deterioration of a surface layer to be caused by attachment of an active substance such as ozone or $NO_x$ generated at the time of charging the electrophotographic photoreceptor and can enhance the durability of the electrophotographic photoreceptor at the time of being repeatedly used. Further, stability of a coating solution for forming the photosensitive layer to be described below is enhanced, to thereby extend a service life of the coating solution. The electrophotographic photoreceptor produced by using the coating solution also have an enhanced durability because of a reduced amount of an impurity.

Examples of such antioxidants include hindered phenol derivatives and hindered amine derivatives. An amount of the antioxidant to be used is not particularly limited and is, based on 100 parts by weight of the charge transporting substance, preferably in the range of from 0.1 to 10 parts by weight. When the amount of the antioxidant to be used in less than 0.1 part by weight, enhancement effects of the stability of the coating solution for forming the photosensitive layer to be described below and the durability of the electrophotographic photoreceptor come to be insufficient. Further, when it is more than 10 parts by weight, detrimental effects are given to the electric properties of the electrophotographic photoreceptor.

The photosensitive layer 2 can be formed by firstly preparing a coating solution for forming the photosensitive layer by dissolving and/or dispersing the charge generating substance, the asymmetric bis-hydroxyenamine compound according to the invention and the binder resin and, optionally, the charge transporting substance other than the asymmetric bis-hydroxyenamine compound according to the invention, the antioxidant and the like in an appropriate organic solvent and, then, applying the thus-prepared coating solution on a surface of a conductive substrate 1 or an intermediate layer 6 to be described below and, thereafter, removing the organic solvent from the thus-applied coating solution by drying. Since the asymmetric bis-hydroxyenamine compound according to the invention is excellent in the solubility in the solvent and compatibility with the binder resin, it can uniformly be dispersed in the coating solution and is not crystallized also in a process of forming the photosensitive layer 2. Therefore, according to the invention, a uniform photosensitive layer 2 being free of a crystallized portion can be formed.

Examples of such organic solvents include aromatic hydrocarbons such as benzene, toluene, xylene, mesitylene, tetralin, diphenyl methane, dimethoxybenzene, and dichlorobenzene; halogenated hydrocarbons such as dichloromethane and dichloroethane; ethers such as tetrahydrofuran (THF), dioxane, dibenzyl ether, and dimethoxy methyl ether; ketones such as cyclohexanone, acetophenone, and isophorone; esters such as methyl benzoate and ethyl acetate; sulfur-containing solvents such as diphenyl sulfide; fluorine-based solvents such as hexafluoroisopropanol; non-protonic polar solvents such as N,N-dimethylformamide; a mixed solvent of two or more of these solvents; and a mixed solvent of one or more of these solvents and any one of alcohols, acetonitrile or methyl ethyl ketone.

Thickness of the photosensitive layer is not limited and is preferably in the range of from 5 to 100 µm and, more preferably from 10 to 50 µm. When the thickness is less than 5 µm, there is a risk of reducing charge retention capacity of the surface of the electrophotographic photoreceptor. When the thickness is more than 100 µm, there is a risk of deteriorating productivity of the electrophotographic photoreceptor.

[Layered Type Photosensitive Layer]

The photosensitive layer 7 which is a layered type photosensitive layer is a laminate constituted by containing the charge generating layer 3 and the charge transporting layer 4.

[Charge Generating Layer]

The charge generating layer 3 contains the charge generating substance and the binder resin.

As for the charge generating substance, one or more of the same charge generating substances as those contained in the photosensitive layer 2 can be used.

As for the binder resin, such substances as ordinarily used as matrix resins of the charge generating layer can be used. Examples thereof include thermoplastic resins such as polyester, polystyrene, acrylic resins, methacrylic resins, polycarbonate, and polyallylate; thermosetting resins such as polyurethane, phenol resins, alkyd resins, melamine resins, epoxy resins, silicone resins, phenoxy resins, polyvinyl butyral, and polyvinyl formal; copolymer resins each having two or more constituent units selected from among those contained in these resins (insulating resins such as a copolymer resin of vinyl chloride-vinyl acetate, a copolymer resin of vinyl chloride-vinyl acetate-maleic anhydride, and a copolymer resin of acrylonitrile-styrene). Among these resins, polyvinyl butyral is preferable. The binder resins may be each used alone, or two or more of the binder resins may be used in combination.

A ratio of the to-be-contained charge generating substance to the to-be-contained binder resin is not particularly limited, and the charge generating substance is contained, based on the entire weight of the charge generating substance and the binder resin, preferably in the range of from 10% by weight to 99% by weight and the rest is occupied by the binder resin. When the ratio of the charge generating substance is less than 10% by weight, there is a risk of reducing the sensitivity, while, when the ratio of the charge generating substance is more than 99% by weight, not only film strength of the charge generating layer 3 is reduced, but also dispersibility of the charge generating substance is deteriorated, to thereby increase the number of coarse particles and decrease surface charges in portions other than the portion to be erased by exposure and therefore, there is a risk of generating an image defect, particularly, image fogging called as a black spot in which a fine black spot is formed to a great extent by allowing a toner to adhere to a white background.

The charge generating layer 3 may contain, besides the above-described two essential components, optionally, at least one type in an appropriate amount selected from among a hole transporting material, an electron transporting material, an antioxidant, a dispersion stabilizer, a sensitizing agent and the like. By performing such containing, not only potential properties are enhanced, but also stability of a coating solution for forming the charge generating layer to be described below can be enhanced, to thereby reduce fatigue deterioration of the electrophotographic photoreceptor at the time of repeated use and therefore, the durability of the electrophotographic photoreceptor can be enhanced.

The charge generating layer 3 can be formed by firstly preparing a coating solution for the charge generating layer by allowing, for example, the charge generating substance, the binder resin and, optionally, other additives to be dissolved or dispersed in an appropriate solvent, coating the thus-prepared coating solution on a surface of a conductive substrate 1 or an intermediate layer 6 to be described below and, then, removing the solvent by drying. Specifically, the coating solution for the charge generating layer is prepared by dissolving or dispersing the charge generating substance and, optionally, other additives in a resin solution in which, for example, the binder resin is dissolved in an organic solvent.

Examples of such organic solvents include halogenated hydrocarbons such as tetrachloropropane, and dichloroethane; ketones such as isophorone, methyl ethyl ketone, acetophenone, and cyclohexanone; esters such as ethyl acetate, methyl benzoate, and butyl acetate; ethers such as tetrahydrofuran (THF), dioxane, dibenzyl ether, and 1,2-dimethoxyethane; aromatic hydrocarbons such as benzene, toluene, xylene, mesitylene, tetralin, diphenyl methane, dimethoxybenzene, and dichlorobenzene; sulfur-containing solvents such as diphenyl sulfide; fluorine-based solvents such as hexafluoroisopropanol; and non-protonic polar solvents such as N,N-dimethylformamide and N,N-dimethylacetamide. Further, these solvents may be used as a mixed solvent in which two or more these solvents are mixed with one another.

Prior to dissolving or dispersing the charge generating substance or the like in the resin solution, the charge generating substance and other additives may be subjected to preliminary grinding. The preliminary grinding is performed by using any one of ordinary grinding machines such as a ball mill, a sand mill, an attritor, a vibrating mill, and an ultrasonic dispersing machine.

Dissolving or dispersing the charge generating substance or the like in the resin solution is performed by using an ordinary dispersing machine such as a paint shaker, a ball mill, or a sand mill. On this occasion, it is preferable to appropriately select dispersion conditions in order to prevent an impurity from being generated from a container holding the resin solution, the charge generating substance or the like and members constituting the dispersing machine by abrasion or the like and, then, mixed in the coating solution.

As for a coating method of the coating solution for forming the charge generating layer, roller coating, spray coating, blade coating, ring coating, and dip coating are mentioned.

Thickness of the charge generating layer 3 is not particularly limited, and is preferably in the range of from 0.05 to 5 µm and, more preferably, from 0.1 to 1 µm. When the thickness thereof is less than 0.05 µm, light absorption efficiency is reduced, to thereby reduce the sensitivity. When the thickness thereof is more than 5 µm, the transfer of the charge inside the charge generating layer comes to be in a rate-controlling step in a process of erasing the charge on a surface of the photographic photoreceptor, to thereby reduce sensitivity.

[Charge Transporting Layer]

The charge transporting layer 4 contains the asymmetric bis-hydroxyenamine compound according to the invention having ability of receiving and transporting the charge generated in the charge generating substance and the binder resin. Further, the charge transporting layer 4 can optionally contain other charge transporting substances than the asymmetric bis-hydroxyenamine compound according to the invention, and an additive such as an antioxidant.

As for the asymmetric bis-hydroxyenamine compound according to the invention, one or more compounds selected from the above-described the asymmetric bis-hydroxyenamine compound (1) can be used.

As for the charge transporting substance other than the asymmetric bis-hydroxyenamine compound according to the invention, the binder resin, and the antioxidant, the same articles as those used in the photosensitive layer 2 can be used in the same amounts, respectively.

The charge transporting layer 4 can be formed by, for example, firstly preparing a coating solution for forming the charge transporting layer by dissolving or dispersing the asymmetric bis-hydroxyenamine compound according to the invention, the binder resin and, optionally, the charge transporting substance other than the asymmetric bis-hydroxyenamine compound according to the invention, the antioxidant and the like in an appropriate organic solvent and, then, applying the thus-prepared coating solution for forming the charge transporting layer on a surface of the charge generating layer 3 and, thereafter, removing the organic solvent by drying. Since the asymmetric bis-hydroxyenamine compound according to the invention is not crystallized also in a process of forming the charge transporting layer 4, according to the invention, the charge transporting layer 4 in which the asymmetric bis-hydroxyenamine compound according to the invention is uniformly dispersed can be formed.

As for the organic solvent to be used on this occasion, the same organic solvents as those used in forming the photosensitive layer 2 can be used. The coating method of the coating solution for forming the charge transforming layer on the surface of the charge generating layer 3 is not particularly limited, and examples of such coating methods include dip coating, roller coating, and inkjet coating. Further, the drying which removes the organic solvent contained in the coating solution can be performed by appropriately selecting the temperature capable of forming the charge transporting layer 4 having a uniform surface.

Thickness of the charge transporting layer 4 is not particularly limited and is, preferably, in the range of from 5 to 50 µm and, more preferably, from 10 to 40 µm. When the thickness of the charge transporting layer is less than 5 µm, there is a risk of deteriorating the charge holding capacity of the surface of the electrophotographic photoreceptor. When the thickness of the charge transporting layer is more than 50 µm, there is a risk of deteriorating resolution of the electrophotographic photoreceptor.

[Surface Protective Layer]

The surface protective layer 5 has a function of enhancing durability of the electrophotographic photoreceptor. The surface protective layer 5 contains the asymmetric bis-hydroxyenamine compound according to the invention and the binder resin. Further, the surface protective layer 5 may, optionally, contains other charge transporting substances than the asymmetric bis-hydroxyenamine compound according to the invention.

As for the asymmetric bis-hydroxyenamine compound according to the invention, one or more compounds selected from the above-described asymmetric bis-hydroxyenamine compounds (1) can be used. Further, as for other charge transporting substances than the asymmetric bis-hydroxyenamine compound according to the invention and the binder resin, the same ones as those used in the photosensitive layer 2 can be used, respectively.

A ratio of the to-be-used asymmetric bis-hydroxyenamine compound according to the invention to the to-be-used binder resin is not particularly limited and, in the surface protective layer 5, the amount of the binder resin to be used is, based on 100 parts by weight of the asymmetric bis-hydroxyenamine compound according to the invention, in the range of from 100 parts by weight to 2000 parts by weight. When the amount of the binder resin to be used is, based on 100 parts by weight of the asymmetric bis-hydroxyenamine compound according to the invention, less than 100 parts by weight, an abrasion amount becomes large and, then, there is a risk of being incapable of bearing a role as the surface protective layer 5. When the amount of the binder resin to be used is more than 2000 parts by weight, there is a risk of reducing the sensitivity.

In the electrophotographic photoreceptor provided with the surface protective layer 5, as for the charge transporting substance to be contained in the photosensitive layer 2 or the charge transporting layer 4, a butadiene compound is preferable. Since, by using the butadiene compound, a potential barrier is prevented from being formed at an interface between the photosensitive layer 2 or the charge transporting layer 4 and the surface protective layer 5, the transfer of the charge between the surface protective layer 5 and the photosensitive layer 2 or the charge transporting layer 4 is smoothly conducted and the sensitivity and light responsiveness of the photoreceptor can be enhanced.

Further, in the electrophotographic photoreceptor provided with the surface protective layer 5, as for the charge transporting substance to be contained in the photosensitive layer 2 or the charge transporting layer 4, the asymmetric bis-hydroxyenamine compound according to the invention may be used. The asymmetric bis-hydroxyenamine compound according to the invention contains a structure similar to the butadiene compound and therefore, in the same manner as in the case in which the butadiene compound is used, the transfer of the charge between the photosensitive layer 2 or the charge transporting layer 4 and the surface protective layer 5 is smoothly conducted, and the sensitivity and light responsiveness of the photoreceptor can be enhanced.

The surface protective layer 5 can be formed by, for example, firstly preparing a coating solution for forming the surface protective layer by dissolving or dispersing the asymmetric bis-hydroxyenamine compound according to the invention, the binder resin and, optionally, the charge transporting substance other than the asymmetric bis-hydroxyenamine compound according to the invention in an appropriate organic solvent and, then, applying the thus-prepared coating solution for forming the surface protective layer on a surface of the photosensitive layer 2 or photosensitive layer 7 and, thereafter, removing the organic solvent by drying. As for the organic solvent to be used on this occasion, the same organic solvents as those used in forming the photosensitive layer 2 can be used. Since crystallization of the asymmetric bis-hydroxyenamine compound according to the invention does not occur even in the process of forming the surface protective layer 5, according to the invention, the surface protective layer 5 in which the asymmetric bis-hydroxyenamine compound according to the invention is uniformly dispersed can be formed.

Thickness of the surface protective layer 5 is not particularly limited and is, preferably, in the range of from 0.5 to 10 µm and, more preferably, from 1 to 5 µm. When the thickness of the surface protective layer 5 is less than 0.5 µm, abrasion resistance of the surface of the electrophotographic photoreceptor is inferior and the durability thereof is insufficient. When the thickness of the surface protective layer 5 is more than 10 µm, resolution of the electrophotographic photoreceptor is reduced.

[Intermediate Layer]

The intermediate layer 6 has a function of preventing injection of charges from the conductive substrate 1 to the photosensitive layer 2 or photosensitive layer 7. As a result, reduction of the charging properties of the photosensitive layer 2 or photosensitive layer 7 is suppressed and generation of an image defect such as fogging is prevented. Particularly, at the time of forming an image by the process of a reverse development, image fogging which is called as a black spot in which a fine black spot based on toner is formed in a white background is prevented from being generated. Further, by covering the surface of the conductive substrate 1 with the intermediate layer 6, an extent of unevenness which is a defect of the surface of the conductive substrate 1 is reduced, uniformity of the surface is realized, film-forming properties of the photosensitive layer 2 or photosensitive layer 7 is enhanced, and an adhesion between the conductive substrate 1 and the photosensitive layer 2 or photosensitive layer 7 can be enhanced.

The intermediate layer 6 can be formed by, for example, firstly preparing a coating solution for forming the intermediate layer by dissolving a resin material in an appropriate solvent, applying the thus-prepared coating solution on a surface of conductive substrate 1 and then removing the solvent in the coating solution by drying. Examples of such resin materials which each constitute a resin layer include thermoplastic resins such as polyethylene, polypropylene, polystyrene, acrylic resins, vinyl chloride resins, vinyl acetate resins, polyester, polycarbonate, polyester carbonate, polysulfone, polyvinyl butyral, polyamide, and polyallylate; thermosetting resins such as polyurethane, epoxy resins, melamine resins, phenoxy resins, and silicone resins; copolymer resins each containing two or more constituent units contained in these thermoplastic or thermosetting resins; and natural polymeric materials such as casein, gelatin, polyvinyl alcohol, and ethyl cellulose. Examples of solvents which dissolve or disperse these resin materials include water, alcohols such as methanol, ethanol, and butanol; glymes such as methyl carbitol and butyl carbitol; and mixed solvents prepared by mixing two or more of these solvents.

Further, a metal oxide particle may be added to the coating solution for forming the intermediate layer. By such addition of the metal oxide particle, volume resistance of the intermediate layer 6 can easily be adjusted, the charge injection from the conductive substrate 1 to the photosensitive layer 2 or photosensitive layer 7 can further be suppressed, and electric properties of the electrophotographic photoreceptor can be maintained in various types of environments. Examples of such metal oxide particles include particles of titanium oxide, aluminum oxide, aluminum hydroxide, and tin oxide. Dispersion of metal oxide fine particles in the coating solution for forming the intermediate layer can be performed by using an ordinary particle dispersing machine such as a ball mill, a sand mill, an attritor, a vibrating mill, or an ultrasonic dispersing machine.

Under the condition that an entire amount of the resin material and the metal oxide particle to be contained in the coating solution for forming the intermediate layer which contains the resin material and the metal oxide particle is defined as C and an amount of the solvent to be contained therein is defined as D, a ratio between them (C/D) is, preferably, from 1/99 to 40/60 (equivalent to from 0.01 to 0.67, by weight ratio) and, more preferably, from 2/98 to 30/70 (equivalent to from 0.02 to 0.43, by weight ratio). Further, a ratio (E/F) of an amount of the to-be-contained resin material (E) to an amount of the to-be-contained metal oxide particle (F) is, preferably, from 1/99 to 90/10 (equivalent to from 0.01 to 9.0, by weight ratio) and, more preferably, from 5/95 to 70/30 (equivalent to from 0.05 to 2.33, by weight ratio).

Thickness of the intermediate layer 6 is not particularly limited and is, preferably, in the range of from 0.01 to 20 µm and, more preferably, from 0.1 to 10 µm. When the thickness of the intermediate layer 6 is less than 0.01 µm, it does not substantially function as the intermediate layer 6, a uniform surface to be produced by covering the defect of the conductive substrate 1 can not be realized, and the charge injection from the conductive substrate 1 to the photosensitive layer 2 or photosensitive layer 7 can not be prevented and therefore, chargeability of the photosensitive layer 2 or photosensitive layer 7 is reduced. When the thickness of the intermediate layer 6 is more than 20 µm, it comes difficult to form the intermediate layer 6 in a uniform manner and, also, sensitivity of the electrophotographic photoreceptor is reduced.

Further, a layer containing alumite may be formed on the surface of the conductive substrate 1 and allowed to be the intermediate layer 6.

Figure 9:
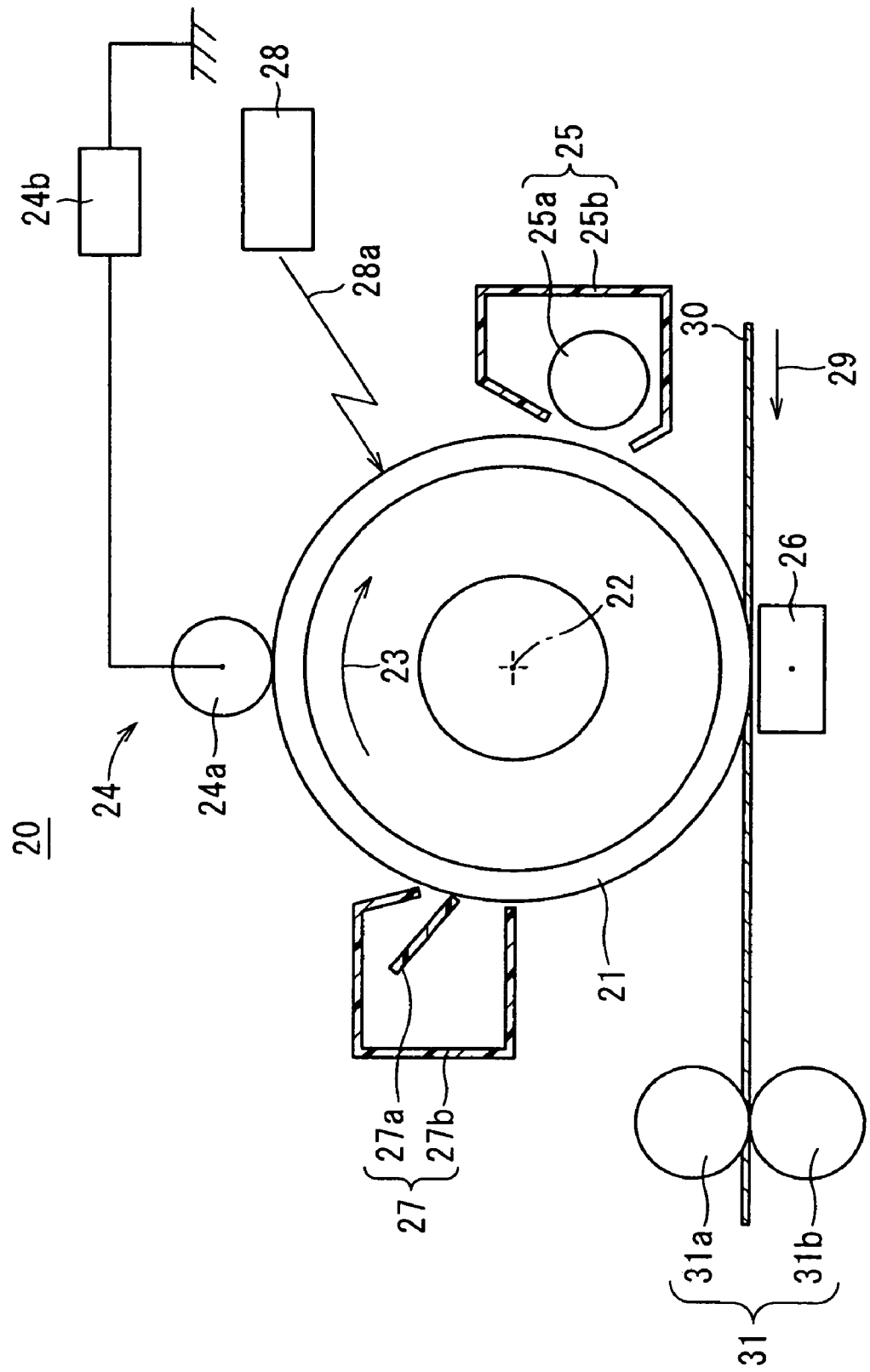
FIG. 9 is a side elevational view for arrangement schematically showing the constitution of an image forming apparatus according to still another embodiment of the invention.

FIG. 9 is a side elevational view for arrangement schematically showing the constitution of an image forming apparatus 20 according to still another embodiment of the invention. The image forming apparatus 20 is characterized by containing an electrophotographic photoreceptor 21 according to the invention having the same constitution as that of any one of the electrophotographic photoreceptors 11 to 18 shown in FIG. 1 to FIG. 8. With reference to FIG. 9, the image forming apparatus 20 which is another embodiment according to the invention will be described. Further, the image forming apparatus according to the invention is not limited to ones described below.

The image forming apparatus 20 is the electrophotographic photoreceptor 21 according to the invention is constituted by containing the electrophotographic photoreceptor 21 which is rotatably supported in the apparatus main body (not shown), a charger 24, exposure means 28, a developing unit 25, a transfer unit 26, a cleaner 27, and a fixing unit 31.

The electrophotographic photoreceptor 21 is rotationally driven in a direction of an arrow mark 23 around a rotation axis line 22. Driving means is constituted by containing, for example, a motor and a reduction gear and then, the electrophotographic photoreceptor 21 is rotationally driven at a given peripheral velocity by conveying a driving force thereof to a conductive substrate which constitutes a core of the electrophotographic photoreceptor 21. The charger 24, the exposure means 28, the developing unit 25, the transfer unit 26 and the cleaner 27 are provided in the stated order from an upstream side to a downstream side of a rotational direction shown by the arrow mark 23, of the electrophotographic photoreceptor 21 along an outer peripheral face of the electrophotographic photoreceptor 21.

The charger 24 is charging means for charging the outer peripheral face of the electrophotographic photoreceptor 21 to a given potential. In the present embodiment, the charger 24 is realized by containing a contact-type charging roller 24a, and a bias power source 24b for applying a voltage to the charging roller 24a. Although a charger wire can also be used as the charging means, in the charging roller in which a high durability of the surface of the photoreceptor is required, the electrophotographic photoreceptor on which the surface protective layer according to the invention is formed, exhibits a large effect due to an enhanced durability thereof.

The exposure means 28 is provided with, for example, a semiconductor laser as a light source and then, exposes the outer peripheral face of the charged electrophotographic photoreceptor 21 in accordance with image information by irradiation of a place between the charger 24 of the electrophotographic photoreceptor 21 and the developing unit 25, with light 28a such as a laser beam, which is outputted from the light source. The light 28a repeatedly scans in a direction, which is a main scanning direction, in which the rotation axis line 22 of the electrophotographic photoreceptor 21 extends and then, along with such scanning, an electrostatic latent image is sequentially formed on the surface of the electrophotographic photoreceptor 21.

The developing unit 25 is developing means for developing by using a developing agent the electrostatic latent image formed on the surface of the electrophotographic photoreceptor 21 by exposure, is placed facing the electrophotographic photoreceptor 21 and provided with a developing roller 25a which supplies toner to the outer peripheral face of the electrophotographic photoreceptor 21 and a casing 25b which not only supports the developing roller 25a rotatably around a rotation axis line which is parallel to the rotation axis line 22 of the electrophotographic photoreceptor 21 but also contains the developing agent containing the toner in an inner space thereof.

The transfer unit 26 is transfer means for transferring a toner image, which is a visible image, formed on the outer peripheral face of the electrophotographic photoreceptor 21 onto a transfer paper 30, which is a recording medium, supplied between the electrophotographic photoreceptor 21 and the transfer unit 26 by transporting means (not shown) from a direction of the arrow mark 29. The transfer unit 26 contains, for example, charging means and is a non-contact type transfer means which transfers the toner image onto the transfer paper 30 by providing a charge having a polarity reverse to that of the toner to the transfer paper 30.

The cleaner 27 is cleaning means for removing and recovering the toner remaining on the outer peripheral face of the electrophotographic photoreceptor 21 after a transfer action by the transfer unit 26, and is provided with a cleaning blade 27a which peels the toner remaining on the outer peripheral face of electrophotographic photoreceptor 21, and a casing 27b for recovering which holds the toner thus peeled by the cleaning blade 27a. Further, this cleaner 27 is provided together with a charge elimination lamp.

Still further, in the image forming apparatus 20, a fixing unit 31, which is fixing means for fixing the transferred image, is provided in the downstream side to which the transfer paper 30 which has passed between the electrophotographic photoreceptor 21 and the transfer unit 26 is transported. The fixing unit 31 contains a heating roller 31a having heating means (not shown), a pressurizing roller 31b which is provided opposite to the heating roller 31a and forms a butting portion by being pressed with the heating roller 31a.

An image forming action by this image forming apparatus 20 is performed as described below. Firstly, when the electrophotographic photoreceptor 21 is driven in the direction of the arrow mark 23 by driving means, the surface of the electrophotographic photoreceptor 21 is uniformly charged to a given potential either of positive or negative by the charging unit 24 which is provided in an upstream side of the rotating direction of the electrophotographic photoreceptor 21 from an image focus point of light 28a by exposure means 28.

Next, the exposure means 28 irradiates the surface of the electrophotographic photoreceptor 21 with the light 28a in accordance with image information. In the electrophotographic photoreceptor 21, a surface charge of a portion irradiated with the light 28a by such exposure is removed and then, a difference between the surface potential of the portion irradiated with the light 28a and that of the portion not irradiated with the light 28a, is generated to thereby form an electrostatic latent image.

The toner is supplied from the developing unit 25 provided in an upstream side of the electrophotographic photoreceptor 21 from the image focus point of the light 28a by the exposure means 28 on the surface of the electrophotographic photoreceptor 21 on which the electrostatic latent image is formed, to thereby develop the electrostatic latent image and form a toner image.

In synchronization with the exposure of the electrophotographic photoreceptor 21, the transfer paper 30 is supplied to a place between the electrophotographic photoreceptor 21 and the transfer unit 26. The charge having the polarity reverse to that of the toner is provided to the thus-provided transfer paper 30 by the transfer unit 26 and then, the toner image formed on the surface of the electrophotographic photoreceptor 21 is transferred onto the transfer paper 30.

The transfer paper 30 on which the toner image is transferred is transported to the fixing unit 31 by the transporting means and, when the transfer paper 30 passes through a butting portion formed between the heating roller 31a and the pressing roller 31b of the fixing unit 31, it is heated and pressed and then, the toner image is fixed on the transfer paper 30, to thereby form a solid image. The transfer paper 30 having the thus-formed image is discharged to outside of the image forming apparatus 20 by the transporting means.

On the other hand, the toner remaining on the surface of the electrophotographic photoreceptor 21 even after the toner image is transferred by the transfer unit 26 is peeled off from the surface of the electrophotographic photoreceptor 21 by the cleaner 27 and then, recovered. The charge of the surface of the electrophotographic photoreceptor 21 from which the toner is removed in such a manner as described above is removed by light emitted from the charge elimination lamp and then, the electrostatic latent image on the surface of the electrophotographic photoreceptor 21 is erased. Thereafter, the electrophotographic photoreceptor 21 is driven in a rotating manner and performs repeatedly a series of actions starting from the charging, to thereby continuously form the image.

Since the image forming apparatus 20 according to the invention is provided with the electrophotographic photoreceptor 21 having the photosensitive layer in which the asymmetric bis-hydroxyenamine compound according to the invention is uniformly dispersed or the surface protective layer, the image of high quality being free of the image defect such as the black spot can be formed.
EXAMPLES
The invention will specifically be described with reference to the following examples and comparative examples.
Production Example 1
In accordance with the following reaction process schemes, an Exemplified Compound No. 1 (compound (1aa)) was produced:
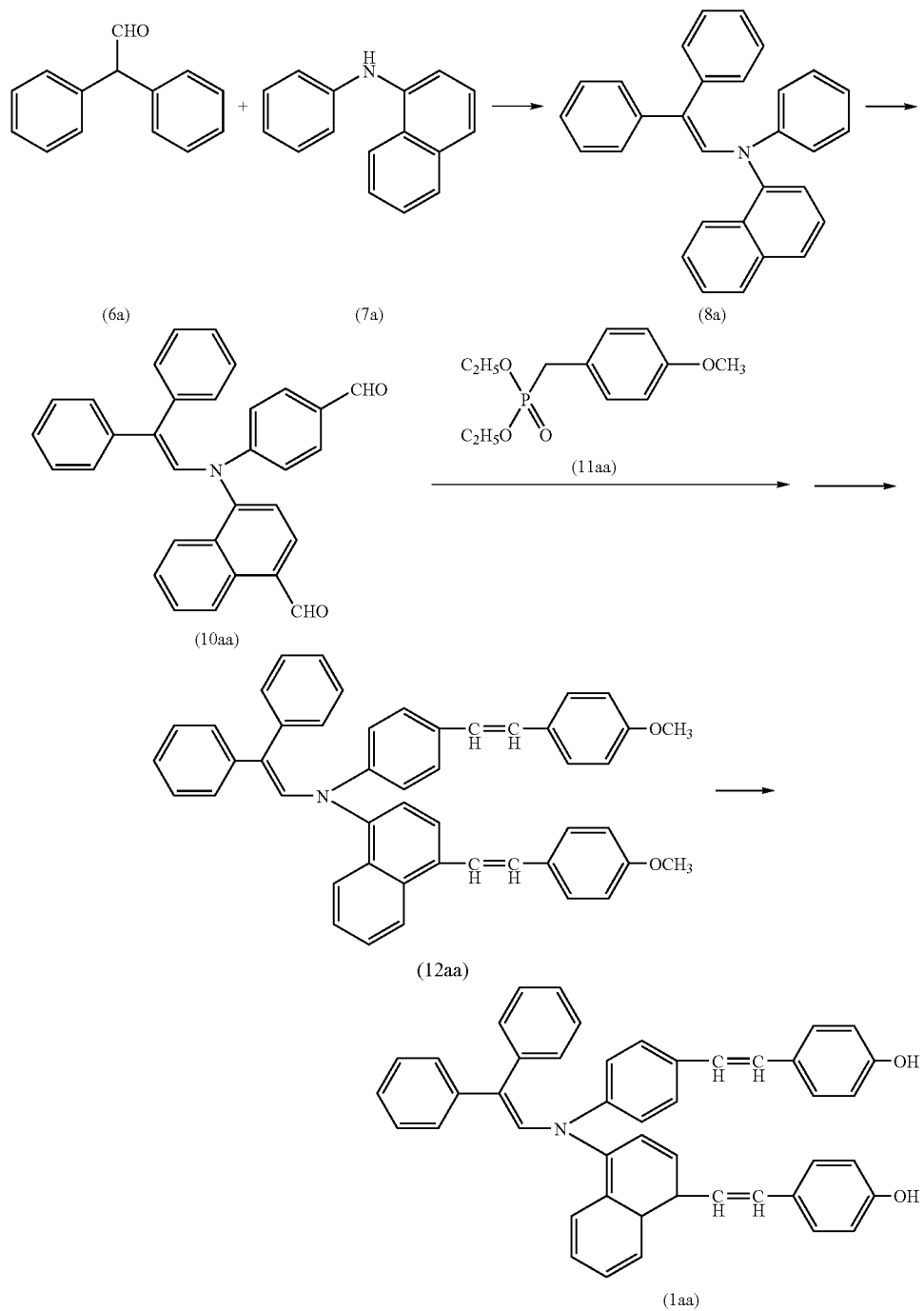

(Production of Enamine Intermediate (8a))

20.6 g (1.05 equivalent weights) of diphenyl acetaldehyde (6a), 21.9 g (1.0 equivalent weight) of N-phenyl-α-naphthylamine (7a), and 0.23 g (0.01 equivalent weights) of DL-10-camphor sulfonic acid were added to 100 ml of toluene and then, the resultant mixture was allowed to react for 6 hours by heating at from 120 to 130° C. while removing by-product water by azeotropic distillation with toluene. After such reaction was terminated, a reaction solution was condensed to about one tenth and then, gradually added in drops into 100 ml of hexane under vigorous stirring, to thereby allow a crystal to be precipitated. The thus-precipitated crystal was filtered out, and rinsed with cold ethanol, to thereby obtain 34.9 g of a pale-yellow powdery compound.

As a result of analyzing the thus-obtained pale-yellow powdery compound by using a liquid chromatography-mass spectrometry (abbreviated as "LC-MS"), a peak corresponding to a molecular ion $[M+H]^+$ in which a proton is added to a compound (calculated molecular weight: 397.18) of a chemical structural formula (8a) was observed at 398.4 and therefore, it was found that the compound was an enamine intermediate (8a) represented by the chemical structural formula (8a) (yield: 88%). Further, from the result of the analysis by the LC-MS, purity of the thus-obtained enamine intermediate (8a) was 99.1%.

[Production of Enamine-Bis-Aldehyde Intermediate (10aa)]

18.4 g (2.4 equivalent weights) of phosphorus oxychloride was gradually added to 100 ml of N,N-dimethylformamide anhydrous (abbreviated as "DMF") and then, stirred for about 30 minutes, to thereby prepare a Vilsmeier reagent. Then, 19.9 g (1.0 equivalent weight) of the enamine intermediate (8a) was gradually added to the reagent while being cooled with ice. Thereafter, the resultant mixture was gradually heated until it had a reaction temperature of 110° C. and stirred for 3 hours while keeping the reaction temperature of 110° C. under heat. After such reaction was terminated, the resultant reaction solution was left to stand for cooling and, then, was gradually added into 800 ml of an aqueous cold 4N sodium hydroxide solution, to thereby allow a crystal to be precipitated. The thus-precipitated crystal was filtered out, thoroughly rinsed with water and then, recrystallized in a mixed solvent of ethanol and ethyl acetate (ethanol ethyl acetate=8:2 to 7:3), to thereby obtain 19.2 g of a pale-yellow powdery compound.

As a result of analyzing the thus-obtained pale-yellow powdery compound by the LC-MS, a peak corresponding to a molecular ion $[M+H]^+$ in which a proton is added to a compound (calculated molecular weight: 453.17) of a chemical structural formula (10aa) was observed at 454.1 and therefore, it was found that the compound was an enamine-bis-aldehyde intermediate (10aa) represented by the chemical structural formula (10aa) (yield: 85%). Further, from the result of the analysis by the LC-MS, purity of the thus-obtained enamine-bis-aldehyde intermediate (10aa) was 99.2%.

[Production of Asymmetric Bis-Alkoxyenamine Compound (12aa)]

9.08 g (1.0 equivalent weight) of an enamine-bis-aldehyde intermediate (10aa) and 12.41 g (2.4 equivalent weights) of diethylbenzyl phosphate (11aa) were dissolved in 80 ml of DMF anhydrous and then, 5.6 g (2.5 equivalent weights) of potassium t-butoxide was gradually added to the resultant solution at 0° C. Thereafter, the resultant mixture was left to stand for one hour at room temperature and then, heated up to 50° C. and, subsequently, stirred for 5 hours under heat such that the temperature of 50° C. was kept. After the resultant reaction solution was left to stand for cooling, the thus-cooled solution was poured into an excess amount of methanol. A generated precipitate was recovered and then, dissolved in toluene, to thereby prepare a toluene solution. The thus-prepared toluene solution was transferred to a separating funnel, rinsed with water and then, an organic layer was removed. The thus-removed organic layer was dried by using magnesium sulfate. After the organic layer was dried, a solid component was removed from the thus-dried organic layer. The organic layer being free of the solid component was subjected to silica-gel column chromatography, to thereby obtain 11.5 g of a yellow crystal.

As a result of analyzing the thus-obtained yellow crystal by the LC-MS, a peak corresponding to a molecular ion $[M+H]^+$ in which a proton is added to a compound (calculated molecular weight: 661.30) of a chemical structural formula (12aa) was observed at 662.5 and therefore, it was found that the crystal was an asymmetric alkoxyenamine compound (12aa) which is a precursor of the Exemplified Compound No. 1 (yield: 87%). Further, from the result of the analysis by the LC-MS, purity of the thus-obtained compound was 99.7%.

[Synthesis of Asymmetric Bis-Hydroxyenamine Compound (1aa) (Exemplified Compound No. 1)]

7.2 g (1.0 equivalent weight) of an asymmetric bis-alkoxyenamine compound (12aa) and 6.39 g (7.0 equivalent weights) of sodium ethanethiolate were suspended in 130 ml of N,N-dimethylformamide and was gradually heated with stirring in a flow of nitrogen gas and then, foaming started at 130° C. After the foaming is ceased, the resultant reaction solution was further heated to reflux for 4 hours. Then, after the reaction solution was left to stand for being cooled down to room temperature, the reaction solution was poured into 600 ml of water with ice and, thereafter, added with 3.2 ml of concentrated hydrochloric acid under stirring, to thereby neutralize the reaction solution. The resultant solution was subjected to extraction by using 400 ml of ethyl acetate. The resultant extract was rinsed with water, dried by using anhydrous magnesium sulfate which was, then, removed by filtering and, thereafter, a solvent therein was distilled out, to thereby obtain 6.71 g of a crude crystal. Subsequently, the crude crystal was recrystallized in a mixed solvent of ethanol and ethyl acetate (ethanol:ethyl acetate=8:2 to 7:3), to thereby obtain 5.91 g of a yellow powdery compound.

Elementary analytical values of the yellow powdery compound by a carbon (C), hydrogen (H) and nitrogen (N) simultaneous quantitative procedure on the basis of a differential specific thermal conductivity method were as follows:

<Elementary Analytical Values of Exemplified Compound No. 1>

Theoretical Values

C: 86.90% H: 5.87% N: 2.20%

Actually Measured Values

C: 86.17% H: 5.24% N: 2.04%

Further, as a result of analyzing the thus-obtained yellow powdery compound by using the LC-MS, a peak corresponding to a molecular ion $[M+H]^+$ in which a proton is added to a compound (calculated molecular weight: 635.28) represented by an intended chemical structural formula (1aa) was observed at 636.7.

From the result of the analysis by the elementary analysis and the LC-MS, it was found that the thus-obtained yellow powdery compound was an asymmetric bis-hydroxyenamine compound (1aa) which was the Exemplified Compound No. 1 (yield: 85%). Further, from the result of the analysis by the LC-MS, purity of the thus-obtained compound (1aa) was 99.1%.

Production Example 2

Synthesis of Symmetric Bis-Hydroxyenamine Compound for Comparison

In the same manner as in Production Example 1 except for using 16.9 g (1.0 equivalent weight) of diphenyl amine as a secondary amine compound in place of 21.9 g (1.0 equivalent weight) of N-phenyl-α-naphthylamine (7a), obtained was 4.21 g of a symmetric bis-hydroxyenamine compound (hereinafter, referred to also as "symmetric bis-hydroxyenamine compound (13)") represented by the following chemical structural formula (13) which is the exemplified compound (EA-14) as described in Example 1 in JP-A No. 2004-269377:

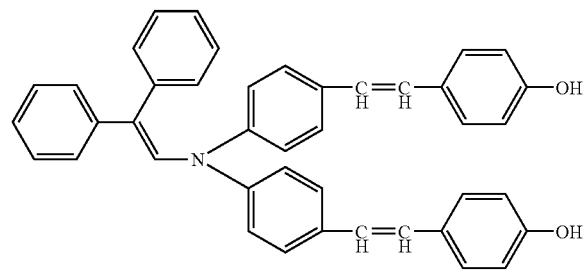

(13)

Elementary analytical values of the thus-obtained symmetric bis-hydroxyenamine compound (13) by a carbon (C), hydrogen (H) and nitrogen (N) simultaneous quantitative procedure on the basis of a differential specific thermal conductivity method were as follows:

<Elementary Analytical Values of Symmetric Bis-Hydroxyenamine Compound (13)>

Theoretical Values
C: 86.42% H: 5.70% N: 2.40%

Actually Measured Values
C: 85.97% H: 5.38% N: 2.27%

Further, as a result of analyzing the thus-obtained symmetric bis-hydroxyenamine compound (13) by using the LC-MS, a peak corresponding to a molecular ion $[M+H]^+$ in which a proton is added to a compound (calculated molecular weight: 583.73) represented by an intended chemical structural formula (13) was observed at 584.9.

From the result of the analysis by the elementary analysis and the LC-MS, it was found that the thus-obtained compound was a symmetric bis-hydroxyenamine compound (13) which was the exemplified compound (EA-14) as described in JP-A No. 2004-269377 (yield: 83%). Further, from the result of the analysis by the LC-MS, purity of the thus-obtained compound (13) was 98.3%.

Example 1

In a manner as described below, an electrophotographic photoreceptor in which the Exemplified Compound No. 1 which is the asymmetric bis-hydroxyenamine compound according to the invention produced in Production Example 1 was used as a charge transporting substance of a charge transporting layer was produced. As for a conductive substrate, an article (hereinafter, referred to also as "aluminum vapor-deposited PET film") in which aluminum is vapor-deposited on a surface of a polyethylene terephthalate (abbreviated as PET) film having a thickness of 100 μm was used.

Seven parts by weight of titanium oxide (trade name: Tipaque TTO55A; manufactured by Ishihara Sangyo Kaisha, Ltd.) and 13 parts by weight of a copolymerized nylon resin (trade name: Amilan CM8000; manufactured by Toray Industries, Inc.) were added to a mixed solvent of 159 parts by weight of methyl alcohol and 106 parts by weight of 1,3-dioxolan and then, subjected to a suspension treatment by a paint shaker for 8 hours, to thereby prepare a coating solution for forming an intermediate layer. Then, the thus-prepared coating solution for forming the intermediate layer was applied to an aluminum surface of the aluminum vapor-deposited PET film which was the conductive substrate by using an applicator and then, subjected to natural drying, to thereby form an intermediate layer having a thickness of 1 μm.

Nest, 1 part by weight of an X-type non-metallophthalocyanine and 1 part by weight of a butyral resin (trade name: #6000-C; manufactured by Denki Kagaku Kogyo Kabushiki Kaisha) were mixed with 98 parts by weight of methyl ethyl ketone and then, subjected to a dispersion treatment by a paint shaker, to thereby prepare a coating solution for forming a charge generating layer. The thus-prepared charge generating layer was applied to a surface of the previously-formed intermediate layer in the same manner as in the intermediate layer and then, subjected to air drying, to thereby form a charge generating layer having a thickness of 0.4 μm.

Next, 100 parts by weight of the asymmetric bis-hydroxyenamine compound of the Exemplified Compound No. 1 produced in Production Example 1 and 100 parts by weight of a polycarbonate resin (trade name: Iupilon Z400; manufactured by Mitsubishi Gas Chemical Company, Inc.) were mixed with each other and then, the resultant mixture was dissolved in toluene as a solvent, to thereby prepare a coating solution for forming a charge transporting layer having a solid content of 10%. Subsequently, the thus-prepared coating solution for forming the charge transporting layer was applied to a surface of the previously-formed charge generating layer in the same manner as in the intermediate layer and then, dried for one hour at 110° C., to thereby form a charge transporting layer having a thickness of 20 μm. In such a manner as described above, a layered type electrophotographic photoreceptor according to the invention having a laminate structure in which the intermediate layer, the charge generating layer, and the charge transporting layer were laminated on the conductive substrate in the stated order was produced in the same manner as in the electrophotographic photoreceptor 17 as shown in FIG. 7.

Example 2

In a manner as described below, an electrophotographic photoreceptor in which the Exemplified Compound No. 1 that is the asymmetric bis-hydroxyenamine compound according to the invention produced in Production Example 1 was used as a charge transporting substance of a surface protective layer was produced.

An intermediate layer having a thickness of 1 μm and a charge generating layer having a thickness of 0.4 μm were formed in the stated order on an aluminum surface of a conductive substrate in which aluminum was vapor-deposited on a surface of a PET film having a thickness of 100 μm in the same manner as in Example 1.

Next, a charge transporting layer was formed in the same manner as in Example 1 except for using a butadiene compound (1,1-bis(p-diethylaminophenyl)-4,4-diphenyl-1,3-butadiene (trade name: T405; manufactured by Takasago Chemical Co.) represented by the following chemical structural formula (14) in place of the Exemplified Compound No. 1 which was the asymmetric bis-hydroxyenamine compound according to the invention. Note that hereinafter, the butadiene compound represented by the chemical structural formula (14) is referred to also as "butadiene compound (14)":

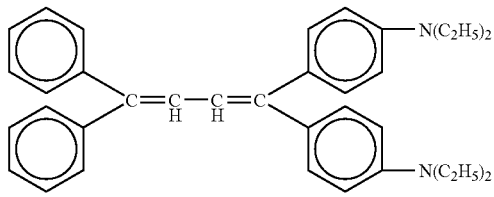

(14)

Next, 60 parts by weight of a hardenable siloxane resin (trade name: KP-854; manufactured by Shin-Etsu Chemical Co., Ltd.) and 60 parts by weight of isopropanol were mixed with each other and allowed to be uniformly dissolved therebetween and then, the resultant solution was added with 6 parts by weight of the asymmetric bis-hydroxyenamine compound which is the Exemplified Compound No. 1 produced in Production Example 1, to thereby prepare a coating solution for forming a surface protective layer. The thus-prepared coating solution for forming the surface protective layer was applied to the surface of the charge transporting layer in the same manner as in the case of forming the intermediate layer in Example 1, and dried for 1 hour at 120° C., to thereby form the surface protective layer having a thickness of 1 μm. In such a manner as described above, a layered type electrophotographic photoreceptor according to the invention having a laminate structure in which the intermediate layer, the charge generating layer, and the charge transporting layer were laminated on the conductive substrate in the stated order, was produced in the same manner as in the electrophotographic photoreceptor 18 as shown in FIG. 8.

Comparative Example 1

A layered type electrophotographic photoreceptor was produced in the same manner as in Example 1 except for using the symmetric bis-hydroxyenamine compound (13) produced in Example 2 in place of the Exemplified Compound No. 1 which was the asymmetric bis-hydroxyenamine compound according to the invention, at the time of forming the charge transporting layer.

<Evaluation of Electric Properties>

With reference to respective electrophotographic photoreceptors obtained in Examples 1 and 2, and Comparative Example 1, electric properties were evaluated by using an electrostatic paper testing apparatus (trade name: EPA-8200; manufactured by Kawaguchi Electric Works Co., Ltd.) in a manner as described below.

The surface of the photoreceptor is charged by applying a voltage of minus (−) 5 kv on the photoreceptor and then, the surface potential of the photoreceptor at this occasion was measured as a charged potential V0 [V]. Next, the thus-charged surface of the photoreceptor was exposed and an exposure amount required for reducing the surface potential of the photoreceptor by half from the charged potential V0 was measured as an exposure amount for reduction by half $E_{1/2}$ [μJ/cm$^2$]. Further, the surface potential of the photoreceptor at the time 10 seconds have passed since the start of the exposure was measured as a remaining potential Vr [V]. Still further, for exposure, light having a wavelength of 780 nm and an intensity of 1 μW/cm$^2$ which was obtained by spectroscopy using a monochrometer was used.

<Evaluation of Image>

With reference to respective electrophotographic photoreceptors obtained in Examples 1 and 2, and Comparative Example 1, conditions of images formed as described below were evaluated.

A photoreceptor drum was taken out of a commercial digital copying machine (trade name: LIBRE AR-451; manufactured by Sharp Corporation), a portion of a photosensitive layer of the photoreceptor drum was peeled off and then, the electrophotographic photoreceptor obtained in each of Examples 1 and 2, and Comparative Example 1 was attached to the portion of the photosensitive layer which was previously peeled off and, thereafter, the resultant photoreceptor drum was set again to the copying machine AR-451. Note that at the time of attaching the electrophotographic photoreceptor obtained in each of Examples 1 and 2, and Comparative Example 1, conduction between an aluminum vapor-deposited face of the aluminum vapor-deposited PET film and a conductive substrate of the photoreceptor drum taken out of the copying machine AR-451 was realized by using an aluminum foil and, further, in order to prevent leakage in the developing apparatus, a surface of a conductive portion thereof was covered and protected.

By using the copying machine, a half-tone image was formed on an A3-sized paper defined by JIS P0138 (1998) and was determined as an image for evaluation. The term "half-tone image" as used herein means an image in which density is shown in gradation sequence by black and white dots. The thus-obtained image for evaluation was visually observed and then, image conditions of portions formed by the electrophotographic photoreceptors obtained in Examples 1 and 2, and Comparative Example 1 were evaluated.

The evaluation results thus obtained are shown in Table 10.

TABLE 10

| | Charge transporting layer | Surface protective layer | | | | | |
|---|---|---|---|---|---|---|---|
| | Charge transporting substance | Present or absent | Charge transporting substance | V0 [V] | $E_{1/2}$ [μJ/cm$^2$] | Vr [V] | Image condition |
| Example 1 | Exemplified Compound No. 1 | Absent | — | −580 | 0.15 | −10 | Favorable |
| Example 2 | Butadiene compound (14) | Present | Exemplified Compound No. 1 | −585 | 0.20 | −15 | Favorable |

TABLE 10-continued

| | Charge transporting layer | Surface protective layer | | | | | |
|---|---|---|---|---|---|---|---|
| | Charge transporting substance | Present or absent | Charge transporting substance | V0 [V] | $E_{1/2}$ [µJ/cm$^2$] | Vr [V] | Image condition |
| Comparative Example 1 | Asymmetric bis-hydroxyenamine compound (13) | Absent | — | −580 | 0.22 | −25 | Many black spots |

It was found that the photoreceptors in Example 1 in which the asymmetric bis-hydroxyenamine compound according to the invention was used in the charge transporting layer and Example 2 in which the asymmetric bis-hydroxyenamine compound according to the invention was used in the surface protective layer were each excellent in sensitivity and responsiveness because of a smaller exposure light amount for reduction by half $E_{1/2}$ and a smaller absolute value of remaining potential Vr than those of Comparative Example 1.

Further, in Example 1 and Example 2, image conditions were favorable and an image defect such as a black spot, a washing-out portion, a black streak, or an image blur was not generated. On the contrary, in Comparative Example 1 in which the asymmetric bis-hydroxyenamine compound (13) was used in the charge transporting layer, many black spots were generated in the image. The reason for it, it is considered, is that, since the symmetric bis-hydroxyenamine compound (13) has a high chemical structural symmetry, the compound (13) is low in solubility in a solvent and then, an insoluble portion to the solvent remains in a state of crystal in the charge transporting layer and, thereafter, the portion is exhibited as a black spot in the image.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An electrophotographic photoreceptor comprising:
a conductive substrate; and
a photosensitive layer provided on the conductive substrate, said photosensitive layer comprising a polymeric photoconduction material, said photoconduction material containing as a polymerized monomer an asymmetric bis-hydroxyenamine compound represented by the following general formula (1):

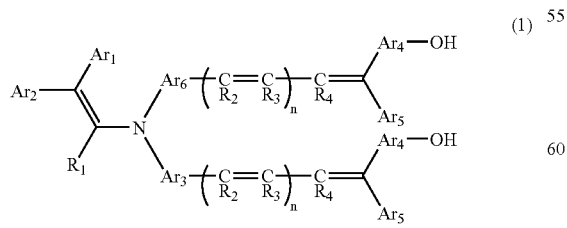

(1)

wherein Ar$_1$ and Ar$_2$ each may be the same or different, and each represent an aryl group which may have a substituent or a heterocyclic group which may have a substituent; Ar$_3$ represents an arylene group which may have a substituent or a divalent heterocyclic group which may have a substituent; two Ar$_4$s each may be the same or different, and each represent an arylene group which may have a substituent or a divalent heterocyclic group which may have a substituent; two Ar$_5$s each may be the same or different, and each represent a hydrogen atom, an aryl group which may have a substituent, a heterocyclic group which may have a substituent, an aralkyl group which may have a substituent, or an alkyl group which may have a substituent; Ar$_6$ represents an arylene group which may have a substituent or a divalent heterocyclic group which may have a substituent; R$_1$ represents a hydrogen atom or an alkyl group which may have a substituent; 2n number of R$_2$s and R$_3$s and two R$_4$s each may be the same or different, and each represent a hydrogen atom, an alkyl group which may have a substituent, an aryl group which may have a substituent, a heterocyclic group which may have a substituent, or an aralkyl group which may have a substituent; two pieces of "n"s may be the same or different, and each represent an integer of from 0 to 3; and Ar$_3$ and Ar$_6$ are not be same with each other.

2. An image forming apparatus comprising:
the electrophotographic photoreceptor of claim 1;
charging means for charging the electrophotographic photoreceptor;
exposure means for exposing the charged electrophotographic photoreceptor to light; and
developing means for developing an electrostatic latent image formed by the exposure.

3. An electrophotographic photoreceptor comprising:
a conductive substrate;
a photosensitive layer provided on the conductive substrate; and
a surface protective layer provided on the conductive substrate, said surface protective layer comprising as a polymerized monomer an asymmetric bis-hydroxyenamine compound represented by the following general formula (1):

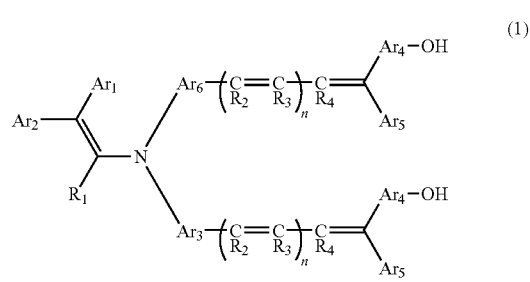

(1)

wherein $Ar_1$ and $Ar_2$ each may be the same or different, and each represent an aryl group which may have a substituent or a heterocyclic group which may have a substituent; $Ar_3$ represents an arylene group which may have a substituent or a divalent heterocyclic group which may have a substituent; two $Ar_4$s each may be the same or different, and each represent an arylene group which may have a substituent or a divalent heterocyclic group which may have a substituent; two $Ar_5$s each may be the same or different, and each represent a hydrogen atom, an aryl group which may have a substituent, a heterocyclic group which may have a substituent, an aralkyl group which may have a substituent, or an alkyl group which may have a substituent; $Ar_6$ represents an arylene group which may have a substituent or a divalent heterocyclic group which may have a substituent; $R_1$ represents a hydrogen atom or an alkyl group which may have a substituent; 2n number of $R_2$s and $R_3$s and two $R_4$s each may be the same or different, and each represent a hydrogen atom, an alkyl group which may have a substituent, an aryl group which may have a substituent, a heterocyclic group which may have a substituent, or an aralkyl group which may have a substituent; two pieces of "n"s may be the same or different, and each represent an integer of from 0 to 3; and $Ar_3$ and $Ar_6$ are not be same with each other.

4. An image forming apparatus comprising:
the electrophotographic photoreceptor of claim 3;
charging means for charging the electrophotographic photoreceptor;
exposure means for exposing the charged electrophotographic photoreceptor to light; and
developing means for developing an electrostatic latent image formed by the exposure.

5. The electrophotographic photoreceptor of claim 1 or claim 3 wherein the asymmetric bis-hydroxyenamine compound represented by the general formula (1) is an asymmetric bis-hydroxyenamine compound represented by the following general formula (2):

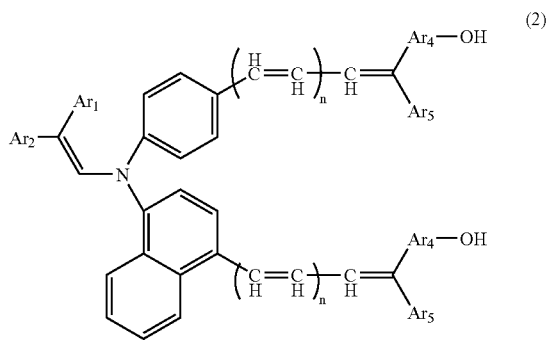

(2)

wherein $Ar_1$ and $Ar_2$ each may be the same or different, and each represent an aryl group which may have a substituent or a heterocyclic group which may have a substituent; two $Ar_4$s each may be the same or different, and each represent an arylene group which may have a substituent or a divalent heterocyclic group which may have a substituent; two $Ar_5$s each may be the same or different, and each represent a hydrogen atom, an aryl group which may have a substituent, a heterocyclic group which may have a substituent, an aralkyl group which may have a substituent, or an alkyl group which may have a substituent; and two pieces of "n"s may be the same or different, and each represent an integer of from 0 to 3.

6. The electrophotographic photoreceptor of claim 1 or claim 3 wherein the wherein the asymmetric bis-hydroxyenamine compound represented by the general formula (1) is an asymmetric bis-hydroxyenamine compound represented by the following general formula (3):

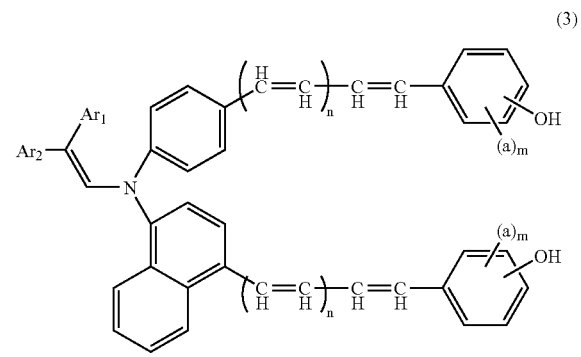

(3)

wherein $Ar_1$ and $Ar_2$ each may be the same or different, and each represent an aryl group which may have a substituent or a heterocyclic group which may have a substituent; two pieces of "n"s may be the same or different, and each represent an integer of from 0 to 3; 2m pieces of "a"s may be the same or different, and each represent an alkyl group which may have a substituent, an alkoxy group which may have a substituent, a dialkylamino group which may have a substituent, an aryl group which may have a substituent, a halogen atom, or a hydrogen atom; 2m pieces of "a"s may form monovalent condensed ring groups together with respective hydroxyphenyl groups to which the 2m pieces of "a"s are bonded; and two pieces of "m"s may be the same or different, and each represent an integer of from 1 to 4.

7. The electrophotographic photoreceptor of claim 1 or claim 3
wherein the asymmetric bis-hydroxyenamine compound represented by the general formula (1) is an asymmetric bis-hydroxyenamine compound represented by the following general formula (4):

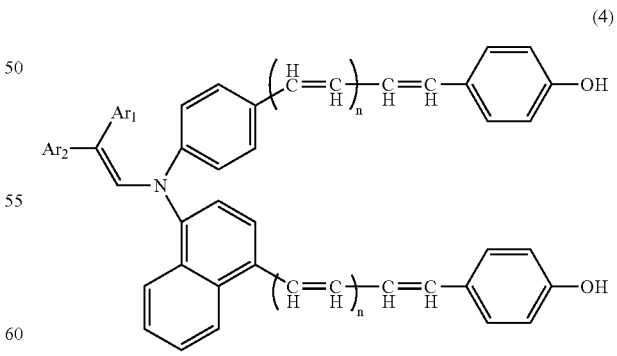

(4)

wherein $Ar_1$ and $Ar_2$ each may be the same or different, and each represent an aryl group which may have a substituent or a heterocyclic group which may have a substituent; and two pieces of "n"s may be the same or different, and each represent an integer of from 0 to 3.

8. The electrophotographic photoreceptor of claim 1 or claim 3 wherein the asymmetric bis-hydroxyenamine compound represented by the general formula (1) is an asymmetric bis-hydroxyenamine compound represented by the following general formula (5):

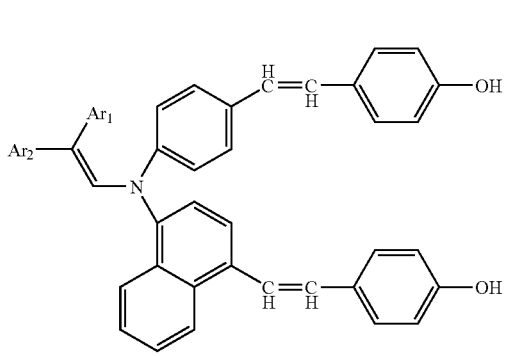

(5)

wherein Ar₁ and Ar₂ each may be the same or different, and each represent an aryl group which may have a substituent or a heterocyclic group which may have a substituent.

9. A polymerized product selected from a polycarbonate, a polyether, a polyester or a polyurethane comprising as a polymerized monomer an asymmetric bis-hydroxyenamine compound represented by the following general formula (1):

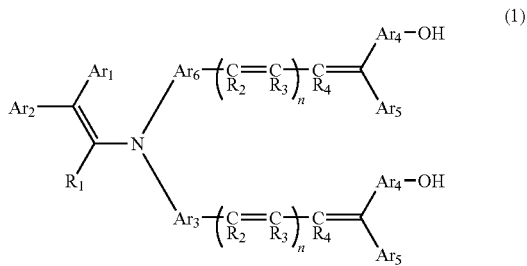

(1)

wherein Ar₁ and Ar₂ each may be the same or different, and each represent an aryl group which may have a substituent or a heterocyclic group which may have a substituent; Ar₃ represents an arylene group which may have a substituent or a divalent heterocyclic group which may have a substituent; two Ar₄s each may be the same or different, and each represent an arylene group which may have a substituent or a divalent heterocyclic group which may have a substituent; two Ar₅s each may be the same or different, and each represent a hydrogen atom, an aryl group which may have a substituent, a heterocyclic group which may have a substituent, an aralkyl group which may have a substituent, or an alkyl group which may have a substituent; Ar₆ represents an arylene group which may have a substituent or a divalent heterocyclic group which may have a substituent; R₁ represents a hydrogen atom or an alkyl group which may have a substituent; 2n number of R₂s and R₃s and two R₄s each may be the same or different, and each represent a hydrogen atom, an alkyl group which may have a substituent, an aryl group which may have a substituent, a heterocyclic group which may have a substituent, or an aralkyl group which may have a substituent; two pieces of "n"s may be the same or different, and each represent an integer of from 0 to 3; and Ar₃ and Ar₆ are not be same with each other.

10. The polymerized product of claim 9 wherein the asymmetric bis-hydroxyenamine compound represented by the general formula (1) is an asymmetric bis-hydroxyenamine compound represented by the following general formula (2):

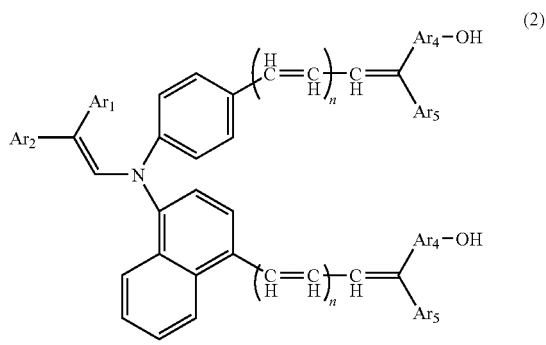

(2)

wherein Ar₁ and Ar₂ each may be the same or different, and each represent an aryl group which may have a substituent or a heterocyclic group which may have a substituent; two Ar₄s each may be the same or different, and each represent an arylene group which may have a substituent or a divalent heterocyclic group which may have a substituent; two Ar₅s each may be the same or different, and each represent a hydrogen atom, an aryl group which may have a substituent, a heterocyclic group which may have a substituent, an aralkyl group which may have a substituent, or an alkyl group which may have a substituent; and two pieces of "n"s may be the same or different, and each represent an integer of from 0 to 3.

11. The polymerized product of claim 9 wherein the wherein the asymmetric bis-hydroxyenamine compound represented by the general formula (1) is an asymmetric bis-hydroxyenamine compound represented by the following general formula (3):

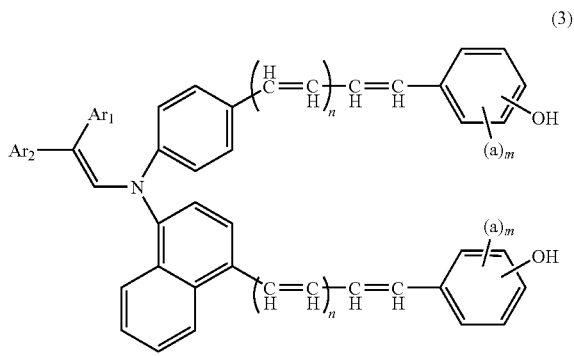

(3)

wherein Ar₁ and Ar₂ each may be the same or different, and each represent an aryl group which may have a substituent or a heterocyclic group which may have a substituent; two pieces of "n"s may be the same or different, and each represent an integer of from 0 to 3; 2m pieces of "a"s may be the same or different, and each represent an alkyl group which may have a substituent, an alkoxy group which may have a substituent, a dialkylamino group which may have a substituent, an aryl group which may have a substituent, a halogen atom, or a hydrogen atom; 2m pieces of "a"s may form monovalent condensed ring groups together with respective hydroxyphenyl groups to which the 2m pieces of "a"s are bonded; and two pieces of "m"s may be the same or different, and each represent an integer of from 1 to 4.

12. The polymerized product of claim 9 wherein the asymmetric bis-hydroxyenamine compound represented by the general formula (1) is an asymmetric bis-hydroxyenamine compound represented by the following general formula (4):

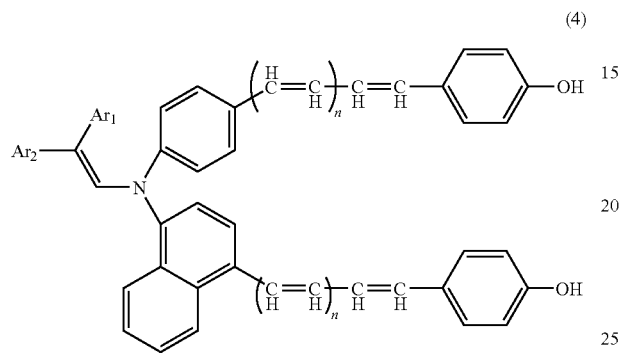

(4)

wherein $Ar_1$ and $Ar_2$ each may be the same or different, and each represent an aryl group which may have a substituent or a heterocyclic group which may have a substituent; and two pieces of "n"s may be the same or different, and each represent an integer of from 0 to 3.

13. The polymerized product of claim 9 wherein the asymmetric bis-hydroxyenamine compound represented by the general formula (1) is an asymmetric bis-hydroxyenamine compound represented by the following general formula (5):

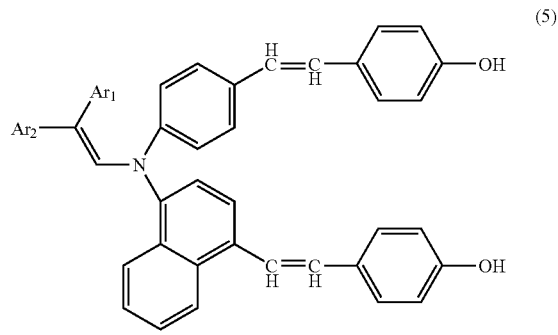

(5)

wherein $Ar_1$ and $Ar_2$ each may be the same or different, and each represent an aryl group which may have a substituent or a heterocyclic group which may have a substituent.

* * * * *